(12) United States Patent
Butler et al.

(10) Patent No.: US 10,829,763 B2
(45) Date of Patent: Nov. 10, 2020

(54) TMPRSS6 IRNA COMPOSITIONS AND METHODS OF USE THEREOF

(71) Applicant: Alnylam Pharmaceuticals, Inc., Cambridge, MA (US)

(72) Inventors: James Butler, Lynnfield, MA (US); Martin A. Maier, Belmont, MA (US); Kevin Fitzgerald, Brookline, MA (US); Shannon Fishman, Cambridge, MA (US); Donald Foster, Attleboro, MA (US); Vasant R. Jadhav, Sharon, MA (US); Stuart Milstein, Arlington, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/269,666

(22) Filed: Feb. 7, 2019

(65) Prior Publication Data
US 2019/0284562 A1 Sep. 19, 2019

Related U.S. Application Data

(60) Division of application No. 15/603,560, filed on May 24, 2017, now Pat. No. 10,246,713, which is a continuation of application No. PCT/US2015/062141, filed on Nov. 23, 2015.

(60) Provisional application No. 62/083,691, filed on Nov. 24, 2014.

(51) Int. Cl.
| A61K 48/00 | (2006.01) |
| C07H 21/04 | (2006.01) |
| C12N 15/113 | (2010.01) |
| A61K 31/713 | (2006.01) |
| A61K 45/06 | (2006.01) |

(52) U.S. Cl.
CPC ........ *C12N 15/1137* (2013.01); *A61K 31/713* (2013.01); *A61K 45/06* (2013.01); *C12N 15/1138* (2013.01); *C12Y 304/21* (2013.01); *C12N 2310/14* (2013.01); *C12N 2310/322* (2013.01); *C12N 2310/351* (2013.01); *C12N 2310/353* (2013.01); *C12N 2310/3533* (2013.01); *C12N 2320/31* (2013.01)

(58) Field of Classification Search
CPC .. C12N 15/113; C12N 2310/11; A61K 48/00; A61K 31/713
See application file for complete search history.

(56) References Cited

U.S. PATENT DOCUMENTS

| 9,783,806 B2 | 10/2017 | Butler et al. |
| 10,246,713 B2 | 4/2019 | Butler et al. |
| 2007/0093443 A1 | 4/2007 | Madison et al. |
| 2009/0191263 A1 | 7/2009 | Reich et al. |
| 2009/0192104 A1 | 7/2009 | McSwiggen et al. |
| 2014/0194489 A1 | 7/2014 | Bumcrot et al. |
| 2014/0288158 A1 | 9/2014 | Rajeev et al. |
| 2017/0362594 A1 | 12/2017 | Butler et al. |
| 2018/0087058 A1 | 3/2018 | Butler et al. |

FOREIGN PATENT DOCUMENTS

| EP | 1752536 A1 | 2/2007 |
| WO | WO-98/13526 A1 | 4/1998 |
| WO | WO-1998/013526 A1 | 4/1998 |
| WO | WO-2004/045543 A2 | 6/2004 |
| WO | WO-2009/073809 A2 | 6/2009 |
| WO | WO-2010/033246 A1 | 3/2010 |
| WO | WO-2010/148013 A2 | 12/2010 |
| WO | WO-2012/135246 A2 | 10/2012 |
| WO | WO-2012/177784 A2 | 12/2012 |
| WO | WO-2013/070786 A1 | 5/2013 |
| WO | WO-2014/190157 A1 | 11/2014 |
| WO | WO-2016085852 A1 | 6/2016 |

OTHER PUBLICATIONS

Elbashir et al. (The EMBO Journal, vol. 20, No. 23, pp. 6877-6888, 2001).*
GenBank Acession NM_001130556; Aug. 28, 2012 [online] downloaded from: http://www.ncbi.nlm.nih.gov/nuccore/NM_001130556/ on Jan. 30, 2017.
GenBank Acession CU691658 ; Feb. 23, 2008 [online] downloaded from: http://www.ncbi.nlm.nih.gov/nuccore/CU691658 on Jan. 30, 2017.
GenBank Acession CU013044; Oct. 7, 2008 [online] downloaded from: http://www.ncbi.nlm.nih.gov/nuccore/CU013044/ on Jan. 30, 2017.
GenBank Acession AY358398; Oct. 3, 2003 [online] downloaded from: http://www.ncbi.nlm.nih.gov/nuccore/37181920/ on Jan. 30, 2017.
GenBank Acession CR456446; Oct. 16, 2008 [online] downloaded from: http://www.ncbi.nlm.nih.gov/nuccore/CR456446/ on Jan. 30, 2017.
GenBank Acession HV848938; Nov. 15, 2012 [online] downloaded from: http://www.ncbi.nlm.nih.gov/nuccore/HV848938 on Jan. 30, 2017.
GenBank Acession HV784394; Nov. 15, 2012 [online] downloaded from: http://www.ncbi.nlm.nih.gov/nuccore/HV784394 on Jan. 30, 2017.
GenBank Acession HI141555; Nov. 2, 2010 [online] downloaded from: http://www.ncbi.nlm.nih.gov/nuccore/HI141555 on Jan. 30, 2017.

(Continued)

*Primary Examiner* — Amy H Bowman
(74) *Attorney, Agent, or Firm* — McCarter & English, LLP; Maria Laccotripe Zacharakis; Deborah L. Nagle

(57) ABSTRACT

The invention relates to RNAi agents, e.g., double-stranded RNAi agents, targeting the TMPRSS6 gene, and methods of using such RNAi agents to inhibit expression of TMPRSS6 and methods of treating subjects having a TMPRSS6 associated disorder, e.g., an iron overload associated disorder, such as β-thalassemia or hemochromatosis.

17 Claims, 12 Drawing Sheets

Specification includes a Sequence Listing.

(56) References Cited

OTHER PUBLICATIONS

GenBank Acession GX268669; Aug. 13, 2010 [online] downloaded from: http://www.ncbi.nlm.nih.gov/nuccore/303211976 on Jan. 30, 2017.
GenBank Acession DM472417; Jan. 21, 2010 [online] downloaded from: http://www.ncbi.nlm.nih.gov/nuccore/DM472417 on Jan. 30, 2017.
GenBank Acession DM180171; Aug. 26, 2009 [online] downloaded from: http://www.ncbi.nlm.nih.gov/nuccore/DM180171 on Jan. 30, 2017.
GenBank Acession DM117477; Jun. 18, 2009 [online] downloaded from: http://www.ncbi.nlm.nih.gov/nuccore/DM117477 on Jan. 30, 2017.
GenBank Acession FB762896; Dec. 18, 2008 [online] downloaded from: http://www.ncbi.nlm.nih.gov/nuccore/FB762896 on Jan. 30, 2017.
GenBank Acession DJ429262; Jun. 11, 2008 [online] downloaded from: http://www.ncbi.nlm.nih.gov/nuccore/DJ429262 on Jan. 30, 2017.
GenBank Acession DI008490; Feb. 21, 2008 [online] downloaded from: http://www.ncbi.nlm.nih.gov/nuccore/DI008490 on Jan. 30, 2017.
GenBank Acession DI066240; Feb. 21, 2008 [online] downloaded from: http://www.ncbi.nlm.nih.gov/nuccore/DI066240 on Jan. 30, 2017.
D'Aquino, KE et al., The protein kinase Kin4 inhibits exit from mitosis in response to spindle position defects. Mol Cell. Jul. 22, 2005;19(2):223-34.
Finberg, K et al., Down-regulation of Bmp/Smad signaling by Tmprss6 is required for maintenance of systemic iron homeostasis. Blood. May 6, 2010;115(18):3817-26. doi: 10.1182/blood-2009-05-224808. Epub Mar. 3, 2010.
Lakhal, S et al., Regulation of type II transmembrane serine proteinase TMPRSS6 by hypoxia-inducible factors: new link between hypoxia signaling and iron homeostasis. J Biol Chem. Feb. 11, 2011;286(6):4090-7. Epub Oct. 21, 2010.
Maxon et al., Matriptase-2- and proprotein convertase-cleaved forms of hemojuvelin have different roles in the down-regulation of hepcidin expression. J Biol Chem. Dec. 10, 2010;285(50):39021-8. doi: 10.1074/jbc.M110.183160. Epub Oct. 11, 2010.
Sisay et al., Identification of the first low-molecular-weight inhibitors of matriptase-2. J Med Chem. Aug. 12, 2010;53(15):5523-35. doi: 10.1021/jm100183e.
International Search Report and Written Opinion for International Application No. PCT/US2014/039149, dated Sep. 1, 2014.
Finberg et al. "Tmprss6, An Inhibitor of Hepatic Bmp/Smad Signaling, Is Required for Hepcidin Suppression and Iron Loading in a Mouse Model of ß-Thalassemia," Blood 2010 116:164.
Velasco et al., "Matriptase-2, a membrane-bound mosaic serine proteinase predominantly expressed in human liver and showing degrading activity against extracellular matrix proteins.", J Biol Chem. Oct. 4, 2002;277(40):37637-46.
Ramsay et al. "Matriptase-2 (TMPRSS6): a proteolytic regulator of iron homeostasis," Haematologica. Jun. 2009; 94(6): 840-849.
Finberg et al., "Tmprss6 is a genetic modifier of the Hfe-hemochromatosis phenotype in mice", Blood, Apr. 28, 2011, vol. 117(17) 4590-4599.
Elbashir et al, "Functional anatomy of siRNAs for mediating efficient RNAi in *Drosophila melanogaster* embryo lysate", EMBO J. Dec. 3, 2001; 20(23): 6877-6888.
International Search Report and Written Report from PCT/US2015/062141 dated Mar. 11, 2016.
Reynolds et al., "Rational siRNA design for RNA interference," Nature Biotechnology, vol. 22, pp. 326-330, 2004.
NCBI_NM_153609.2, *Homo sapiens* transmembrane protease, serine 6 (TMPRSS6), mRNA. Nov. 18, 2006. Version available on PRI Apr. 28, 2012 per sequence retreived in International Search Report on May 30, 2012. Retrieved on Feb. 26, 2016 at http://www.ncbi.nlm.nih.gov/nuccore/56682967?sat=15&satkey=9882477.
Maxson et al. ,"Matriptase-2- and Proprotein Convertase-cleaved Forms of Hemojuvelin Have Different Roles in the Down-regulation of Hepcidin Expression," Journal of Biological Chemistry, vol. 285(50): 39021-39028, 2010.
U.S. Appl. No. 15/603,560 U.S. Pat. No. 10,246,713, filed May 24, 2017 Apr. 2, 2019, US 20170362594, Granted.
U.S. Appl. No. 14/947,025 U.S. Pat. No. 9,783,806, filed Nov. 20, 2015 Oct. 10, 2017, US 20160145629, Granted.
U.S. Appl. No. 16/191,579, filed Nov. 15, 2018, US 20190211341, Published.

\* cited by examiner

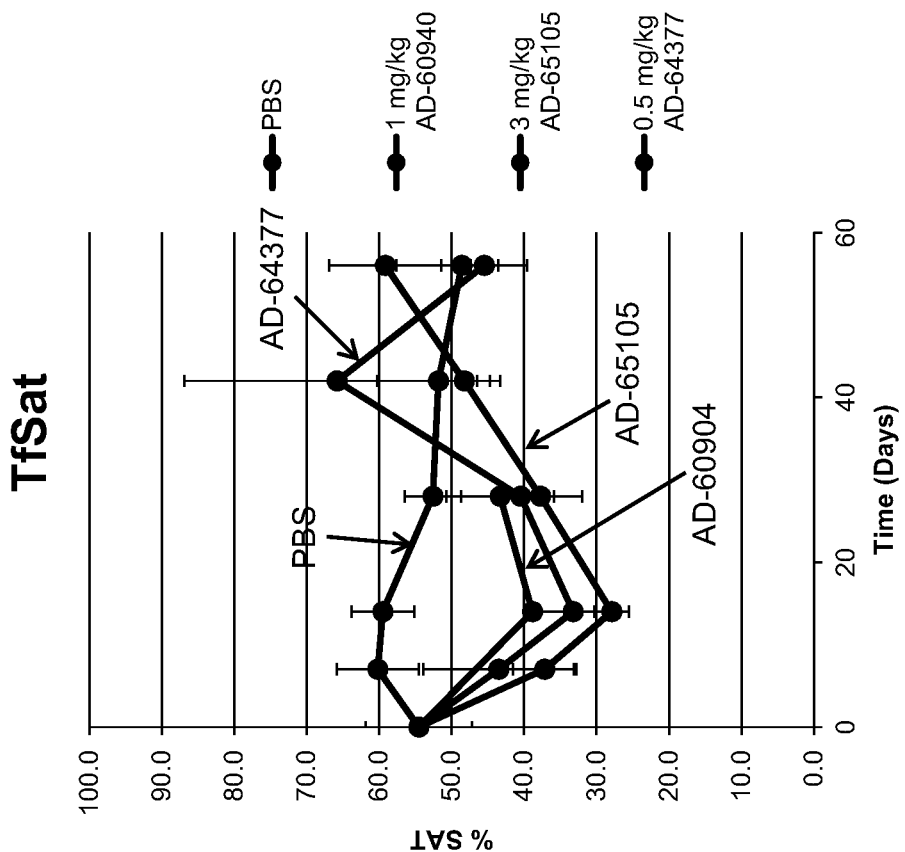
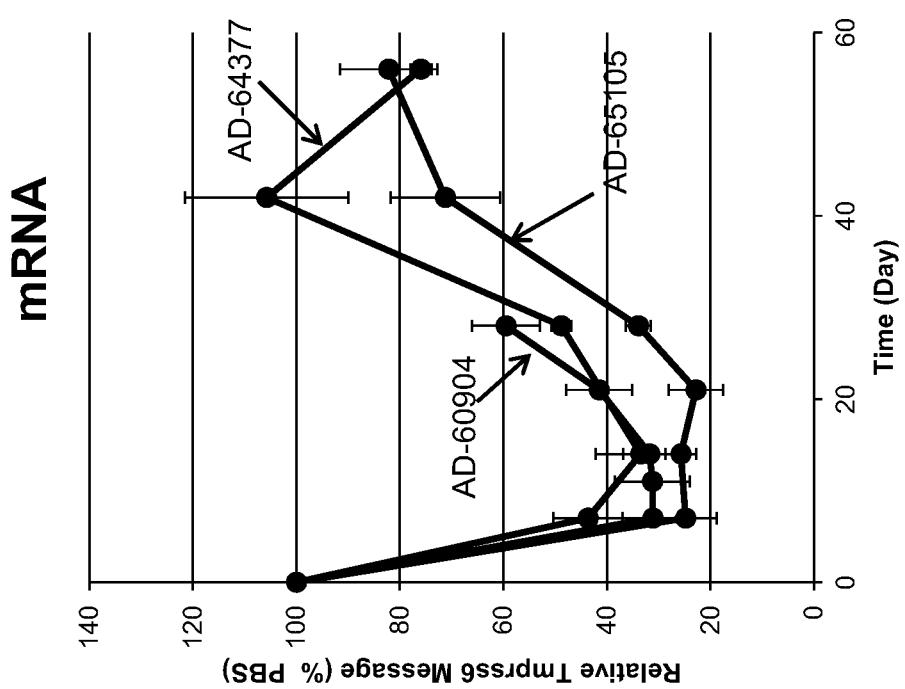
Figure 8B TfSat
Figure 8A mRNA

SEQUENCE LISTING

<160> NUMBER OF SEQ ID NOS: 151

<210> SEQ ID NO 1
<211> LENGTH: 3212
<212> TYPE: DNA
<213> ORGANISM: Homo sapiens

<400> SEQUENCE: 1

| | | | | | |
|---|---|---|---|---|---|
| cttgagccag | acccagtcca | gctctggtgc | ctgccctctg | gtgcgagctg | acctgagatg | 60 |
| cacttccctc | ctctgtgagc | tgtctcggca | cccacttgca | gtcactgccg | cctgatgttg | 120 |
| ttactcttcc | actccaaaag | gatgcccgtg | gccgaggccc | ccaggtggc | tggcgggcag | 180 |
| ggggacggag | gtgatggcga | ggaagcggag | ccggagggga | tgttcaaggc | ctgtgaggac | 240 |
| tccaagagaa | aagcccgggg | ctacctccgc | ctggtgcccc | tgtttgtgct | gctggccctg | 300 |
| ctcgtgctgg | cttcggcggg | ggtgctactc | tggtatttcc | tagggtacaa | ggcggaggtg | 360 |
| atggtcagcc | aggtgtactc | aggcagtctg | cgtgtactca | atcgccactt | ctcccaggat | 420 |
| cttacccgcc | gggaatctag | tgccttccgc | agtgaaaccg | ccaaagccca | gaagatgctc | 480 |
| aaggagctca | tcaccagcac | ccgcctggga | acttactaca | actccagctc | cgtctattcc | 540 |
| tttggggagg | gacccctcac | ctgcttcttc | tggttcattc | tccaaatccc | cgagcaccgc | 600 |
| cggctgatgc | tgagccccga | ggtggtgcag | gcactgctgg | tggaggagct | gctgtccaca | 660 |
| gtcaacagct | cggctgccgt | ccctacagg | gccgagtacg | aagtggaccc | cgagggccta | 720 |
| gtgatcctgg | aagccagtgt | gaaagacata | gctgcattga | attccacgct | gggttgttac | 780 |
| cgctacagct | acgtgggcca | gggccaggtc | ctccggctga | aggggcctga | ccacctggcc | 840 |
| tccagctgcc | tgtggcacct | gcagggcccc | aaggacctca | tgctcaaact | ccggctggag | 900 |
| tggacgctgg | cagagtgccg | ggaccgactg | gccatgtatg | acgtggccgg | gcccctggag | 960 |
| aagaggctca | tcacctcggt | gtacggctgc | agccgccagg | agcccgtggt | ggaggttctg | 1020 |
| gcgtcggggg | ccatcatggc | ggtcgtctgg | aagaagggcc | tgcacagcta | ctacgacccc | 1080 |
| ttcgtgctct | ccgtgcagcc | ggtggtcttc | caggcctgtg | aagtgaacct | gacgctggac | 1140 |
| aacaggctcg | actcccaggg | cgtcctcagc | accccgtact | tccccagcta | ctactcgccc | 1200 |
| caaacccact | gctcctggca | cctcacggtg | ccctctctgg | actacggctt | ggccctctgg | 1260 |
| tttgatgcct | atgcactgag | gaggcagaag | tatgatttgc | cgtgcaccca | gggccagtgg | 1320 |
| acgatccaga | acaggaggct | gtgtggcttg | cgcatcctgc | agcccacgc | cgagaggatc | 1380 |
| cccgtggtgg | ccacggccgg | gatcaccatc | aacttcacct | cccagatctc | cctcaccggg | 1440 |
| cccggtgtgc | gggtgcacta | tggcttgtac | aaccagtcgg | accctgccc | tggagagttc | 1500 |
| ctctgttctg | tgaatggact | ctgtgtccct | gcctgtgatg | gggtcaagga | ctgccccaac | 1560 |
| ggcctggatg | agagaaactg | cgtttgcaga | gccacattcc | agtgcaaaga | ggacagcaca | 1620 |
| tgcatctcac | tgcccaaggt | ctgtgatggg | cagcctgatt | gtctcaacgg | cagcgacgaa | 1680 |
| gagcagtgcc | aggaagggt | gccatgtggg | acattcacct | tccagtgtga | ggaccggagc | 1740 |
| tgcgtgaaga | agcccaaccc | gcagtgtgat | gggcggcccg | actgcaggga | cggctcggat | 1800 |
| gaggagcact | gtgactgtgg | cctccagggc | ccctccagcc | gcattgttgg | tggagctgtg | 1860 |
| tcctccgagg | tgagtggcc | atggcaggcc | agcctccagg | ttcggggtcg | acacatctgt | 1920 |
| gggggggccc | tcatcgctga | ccgctgggtg | ataacagctg | cccactgctt | ccaggaggac | 1980 |
| agcatggcct | ccacggtgct | gtggaccgtg | ttcctgggca | aggtgtggca | gaactcgcgc | 2040 |
| tggcctggag | aggtgtcctt | caaggtgagc | cgcctgctcc | tgcacccgta | ccacgaagag | 2100 |

```
gacagccatg actacgacgt ggcgctgctg cagctcgacc acccggtggt gcgctcggcc    2160
gccgtgcgcc ccgtctgcct gcccgcgcgc tcccacttct tcgagcccgg cctgcactgc    2220
tggattacgg gctggggcgc cttgcgcgag ggcggcccca tcagcaacgc tctgcagaaa    2280
gtggatgtgc agttgatccc acaggacctg tgcagcgagg tctatcgcta ccaggtgacg    2340
ccacgcatgc tgtgtgccgg ctaccgcaag ggcaagaagg atgcctgtca gggtgactca    2400
ggtggtccgc tggtgtgcaa ggcactcagt ggccgctggt tcctggcggg gctggtcagc    2460
tggggcctgg gctgtggccg gcctaactac ttcggcgtct acacccgcat acaggtgtg    2520 atcagctgga tccagcaagt ggtgacctga ggaactgccc ccctgcaaag cagggcccac    2580
ctcctggact cagagagccc agggcaactg ccaagcaggg ggacaagtat tctggcgggg    2640
ggtgggggag agagcaggcc ctgtggtggc aggaggtggc atcttgtctc gtccctgatg    2700
tctgctccag tgatggcagg aggatggaga agtgccagca gctggggagtc aagacgtccc    2760 ctgaggaccc aggcccacac ccagcccttc tgcctcccaa ttctctctcc tccgtcccct    2820
tcctccactg ctgcctaatg caaggcagtg gctcagcagc aagaatgctg ttctacatc    2880 ccgaggagtg tctgaggtgc gccccactct gtacagaggc tgtttgggca gccttgcctc    2940
cagagagcag attccagctt cggaagcccc tggtctaact tgggatctgg gaatggaagg    3000
tgctcccatc ggaggggacc ctcagagccc tggagactgc caggtgggcc tgctgccact    3060
gtaagccaaa aggtggggaa gtcctgactc cagggtcctt gccccacccc tgcctgccac    3120
ctgggccctc acagcccaga ccctcactgg gaggtgagct cagctgccct ttggaataaa    3180
gctgcctgat caaaaaaaaa aaaaaaaaaa aa                                  3212
```

<210> SEQ ID NO 2
<211> LENGTH: 16
<212> TYPE: PRT
<213> ORGANISM: Unknown
<220> FEATURE:
<221> NAME/KEY: source
<223> OTHER INFORMATION: /note="Description of Unknown:
    RFGF peptide"

<400> SEQUENCE: 2

Ala Ala Val Ala Leu Leu Pro Ala Val Leu Leu Ala Leu Leu Ala Pro
1               5                   10                  15

<210> SEQ ID NO 3
<211> LENGTH: 11
<212> TYPE: PRT
<213> ORGANISM: Unknown
<220> FEATURE:
<221> NAME/KEY: source
<223> OTHER INFORMATION: /note="Description of Unknown:
    RFGF analogue peptide"

<400> SEQUENCE: 3

Ala Ala Leu Leu Pro Val Leu Leu Ala Ala Pro
1               5                   10

<210> SEQ ID NO 4
<211> LENGTH: 13
<212> TYPE: PRT
<213> ORGANISM: Human immunodeficiency virus

<400> SEQUENCE: 4

Gly Arg Lys Lys Arg Arg Gln Arg Arg Arg Pro Pro Gln
1               5                   10

<210> SEQ ID NO 5
<211> LENGTH: 16
<212> TYPE: PRT
<213> ORGANISM: Drosophila sp.

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 6
cuuacgcuga guacuucgat t                                              21

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 7
ucgaaguacu cagcguaagt t                                              21

<210> SEQ ID NO 8
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ucugguauuu ccuaggguac a                                              21

<210> SEQ ID NO 9
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
uguacccuag gaaauaccag agu                                            23

<210> SEQ ID NO 10
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
ugguauuucc uaggguacat t                                           21

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
uguacccuag gaaauaccat t                                           21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
ugguauuucc uaggguacat t                                           21

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
ucugguauuu ccuaggguac a                                           21

<210> SEQ ID NO 14
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
cugguauuuc cuaggguaca a                                           21
```

<210> SEQ ID NO 15
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
ggugcuacuc ugguauuucc u                                              21

<210> SEQ ID NO 16
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
cacugugacu guggccucca a                                              21

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
caccucccag aucucccuca a                                              21

<210> SEQ ID NO 18
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ugguauuucc uaggguacaa a                                              21

<210> SEQ ID NO 19
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ccugcccugg agaguuccuc u                                              21

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 20
uguacccuag gaaauaccat t                                              21

<210> SEQ ID NO 21
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
uguacccuag gaaauaccag agu                                            23

<210> SEQ ID NO 22
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
uuguacccua ggaaauacca gag                                            23

<210> SEQ ID NO 23
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
aggaaauacc agaguagcac ccc                                            23

<210> SEQ ID NO 24
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
uuggaggcca cagucacagu gcu                                            23

<210> SEQ ID NO 25
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
uugagggaga ucugggaggu gaa                                            23
```

<210> SEQ ID NO 26
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uuuguacccu aggaaauacc aga                                            23

<210> SEQ ID NO 27
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
agaggaacuc uccagggcag ggg                                            23

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
ugguauuucc uagguacat t                                               21

<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ucugguauuu ccuagggua c a                                             21

<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
cugguauuuc cuaggguaca a                                              21

<210> SEQ ID NO 31
<211> LENGTH: 21
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 31
ggugcuacuc ugguauuucc u                                              21

<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
cacugugacu guggccucca a                                              21

<210> SEQ ID NO 33
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
caccucccag aucucccuca a                                              21

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ugguauuucc uaggguacaa a                                              21

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ccugcccugg agaguuccuc u                                              21

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 36
uguacccuag gaaauaccat t                                              21

<210> SEQ ID NO 37
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
uguacccuag gaaauaccag agu                                            23

<210> SEQ ID NO 38
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 38
uuguacccua ggaaauacca gag                                            23

<210> SEQ ID NO 39
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
aggaaauacc agaguagcac ccc                                            23

<210> SEQ ID NO 40
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
uuggaggcca cagucacagu gcu                                            23

<210> SEQ ID NO 41
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
uugagggaga ucugggaggu gaa                                            23

<210> SEQ ID NO 42
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
uuuguacccu aggaaauacc aga                                           23

<210> SEQ ID NO 43
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
agaggaacuc uccagggcag ggg                                           23

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cugguauuuc cuaggguaca a                                             21

<210> SEQ ID NO 45
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
cugguauuuc cuagggtaca a                                             21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
cugguauuuc cuaggguaca a                                             21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 47
cugguauuuc cuaggguaca a                                              21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
cugguauuuc cuaggguaca a                                              21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
cugguauuuc cuaggguaca a                                              21

<210> SEQ ID NO 50
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 50
cugguauuuc cuagggtaca a                                              21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
cugguauuuc cuaggguaca a                                              21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
cugguauuuc cuaggguaca a                                              21

<210> SEQ ID NO 53
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 53
uuguacccua ggaaauacca gag                                          23

<210> SEQ ID NO 54
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 54
uuguacccua ggaaauacca gag                                          23

<210> SEQ ID NO 55
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 55
uuguacccua ggaaauacca gag                                          23

<210> SEQ ID NO 56
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 56
uuguacccua ggaaauacca gag                                          23

<210> SEQ ID NO 57
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 57
uuguacccua ggaaauacca gag                                          23

<210> SEQ ID NO 58
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

```
<400> SEQUENCE: 58
uuguacccua ggaaauacca gag                                          23

<210> SEQ ID NO 59
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
uuguacccua ggaaauacca gag                                          23

<210> SEQ ID NO 60
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
uuguacccua ggaaauacca gag                                          23

<210> SEQ ID NO 61
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
uuguacccua ggaaauacca gag                                          23

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
cugguauuuc cuaggguaca a                                            21

<210> SEQ ID NO 63
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 63
ncugguauuu ccuaggguac aa                                           22
```

```
<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
cugguauuuc cuaggguaca a                                              21

<210> SEQ ID NO 65
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 65
ncugguauuu ccaggguac aa                                              22

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
cugguauuuc cuaggguaca a                                              21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
cugguauuuc cuaggguaca a                                              21

<210> SEQ ID NO 68
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 68
ncugguauuu ccuaggguac aa                                             22
```

-continued

```
<210> SEQ ID NO 69
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 69
ncugguauuu ccuaggguac aa                                              22

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 70
cugguauuuc cuagggtaca a                                               21

<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 71
cugguauuuc cuagggtaca a                                               21

<210> SEQ ID NO 72
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 72
cugguauuuc cuagggtaca a                                               21

<210> SEQ ID NO 73
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 73
cugguauuuc cuagggtaca a                                              21

<210> SEQ ID NO 74
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 74
cugguauuuc cuagggtaca a                                              21

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
cugguauuuc cuaggguaca a                                              21

<210> SEQ ID NO 76
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
cugguauuuc cuaggguaca a                                              21

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
cugguauuuc cuaggguaca a                                              21

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 78
cugguauuuc cuaggguaca a                                          21

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
cugguauuuc cuaggguaca a                                          21

<210> SEQ ID NO 80
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
cugguauuuc cuaggguaca a                                          21

<210> SEQ ID NO 81
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 81
ncugguauuu ccuagggguac aa                                        22

<210> SEQ ID NO 82
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 82
ncugguauuu ccuagggguac aa                                        22

<210> SEQ ID NO 83
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (1)..(1)
<223> OTHER INFORMATION: 2-hydroxymethyl-tetrahydrofurane-5-phosphate

<400> SEQUENCE: 83
ncugguauuu ccuaggguac aa                                              22

<210> SEQ ID NO 84
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 84
ncugguauuu ccuaggguac aa                                              22

<210> SEQ ID NO 85
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 85
ncugguauuu ccuaggguac aa                                              22

<210> SEQ ID NO 86
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
gguauuuccu aggguacaa                                                  19

<210> SEQ ID NO 87
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
uuguacccua ggaaauacca gag                                             23

<210> SEQ ID NO 88
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 88
uuguacccua ggaaauacca gag                                           23

<210> SEQ ID NO 89
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
uuguacccua ggaaauacca gag                                           23

<210> SEQ ID NO 90
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
uuguacccua ggaaauacca gag                                           23

<210> SEQ ID NO 91
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
uuguacccua ggaaauacca gag                                           23

<210> SEQ ID NO 92
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
uuguacccua ggaaauacca gag                                           23

<210> SEQ ID NO 93
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
uuguacccua ggaaauacca gag                                           23

<210> SEQ ID NO 94
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
uuguacccua ggaaauacca gag                                           23

<210> SEQ ID NO 95
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
uuguacccua ggaaauacca gag                                           23

<210> SEQ ID NO 96
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
uuguacccua ggaaauacca gag                                           23

<210> SEQ ID NO 97
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
uuguacccua ggaaauacca gag                                           23

<210> SEQ ID NO 98
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
uuguacccua ggaaauacca gag                                           23

<210> SEQ ID NO 99
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
```
uuguacccua ggaaauacca gag                                               23

<210> SEQ ID NO 100
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
uuguacccua ggaaauacca gag                                               23

<210> SEQ ID NO 101
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
uuguacccua ggaaauacca gag                                               23

<210> SEQ ID NO 102
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
uuguacccua ggaaauacca gag                                               23

<210> SEQ ID NO 103
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
uuguacccua ggaaauacca gag                                               23

<210> SEQ ID NO 104
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
uuguacccua ggaaauacca gag                                               23

<210> SEQ ID NO 105
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 105
uuguacccua ggaaauacca gag                                              23

<210> SEQ ID NO 106
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
uuguacccua ggaaauacca gag                                              23

<210> SEQ ID NO 107
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
uuguacccua ggaaauacca gag                                              23

<210> SEQ ID NO 108
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
uuguacccua ggaaauacca gag                                              23

<210> SEQ ID NO 109
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
uuguacccua ggaaauacca gag                                              23

<210> SEQ ID NO 110
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
uuguacccua ggaaauacca gag                                              23
```

-continued

```
<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
uuguacccua ggaaauacca g                                          21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
cugguauuuc cuaggguaca a                                          21

<210> SEQ ID NO 113
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 113
cugguauuuc cuagggtaca a                                          21

<210> SEQ ID NO 114
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 114
cugguatuuc cuagggaaca a                                          21

<210> SEQ ID NO 115
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 115
```

-continued cugguatuuc cuagggtaca a                                      21

<210> SEQ ID NO 116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 116
cugguauuuc cuagggtaca a                                      21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
cugguauuuc cuaggguaca a                                      21

<210> SEQ ID NO 118
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 118
ugguatuucc tagggutcaa a                                      21

<210> SEQ ID NO 119
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 119
cugguauuuc cuagggtaca a                                      21

<210> SEQ ID NO 120
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 120
cugguauuuc cuagggtaca a                                              21

<210> SEQ ID NO 121
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 121
cugguauuuc cuagggtaca a                                              21

<210> SEQ ID NO 122
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 122
cugguauuuc cuagggaaca a                                              21

<210> SEQ ID NO 123
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 123
cugguauuuc cuagggaaca a                                              21

<210> SEQ ID NO 124
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 124
```
cugguauuuc cuagggaaca a          21

<210> SEQ ID NO 125
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 125
cugguauuuc cuagggtaca a          21

<210> SEQ ID NO 126
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 126
cugguauuuc cuagggtaca a          21

<210> SEQ ID NO 127
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 127
cugguauuuc cuagggtaca a          21

<210> SEQ ID NO 128
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
uuguacccua ggaaauacca gag          23

<210> SEQ ID NO 129
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

```
<220> FEATURE:
<221> NAME/KEY: source
<223> OTHER INFORMATION: /note="Description of Combined DNA/RNA
      Molecule: Synthetic oligonucleotide"

<400> SEQUENCE: 129
utguacccua ggaaauacca gag                                            23

<210> SEQ ID NO 130
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 130
utguacccua ggaaauacca gag                                            23

<210> SEQ ID NO 131
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 131
uuguacccua ggaaauacca gag                                            23

<210> SEQ ID NO 132
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 132
utguacccua ggaaauacca gag                                            23

<210> SEQ ID NO 133
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
uuguacccua ggaaauacca gag                                            23

<210> SEQ ID NO 134
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 134
utuguaccct aggaaauacc aga                                             23

<210> SEQ ID NO 135
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 135 utgucccua ggaaauacca gag                                              23

<210> SEQ ID NO 136
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 136
uuguacccua ggaaauacca gag                                             23

<210> SEQ ID NO 137
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 137
utguacccua ggaaauacca gag                                             23

<210> SEQ ID NO 138
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 138
utguacccua ggaaauacca gag                                            23

<210> SEQ ID NO 139
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 139
uuguacccua ggaaauacca gag                                            23

<210> SEQ ID NO 140
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 140
utguacccua ggaaauacca gag                                            23

<210> SEQ ID NO 141
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 141
utguacccua ggaaauacca gag                                            23

<210> SEQ ID NO 142
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 142
```
uuguacccua ggaaauacca gag                                              23

<210> SEQ ID NO 143
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 143
utguacccua ggaaauacca gag                                              23

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
ugguauuucc uaggguacaa a                                                21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
ugguauuucc uaggguacaa a                                                21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ugguauuucc uaggguacaa a                                                21

<210> SEQ ID NO 147
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
guauuuccua ggguacaaa                                                   19

<210> SEQ ID NO 148
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
uuuguacccu aggaaauacc aga                                                23

<210> SEQ ID NO 149
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
uuuguacccu aggaaauacc aga                                                23

<210> SEQ ID NO 150
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
uuuguacccu aggaaauacc aga                                                23

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
uuuguacccu aggaaauacc a                                                  21
```

TMPRSS6 IRNA COMPOSITIONS AND METHODS OF USE THEREOF

RELATED APPLICATIONS

This application is a divisional of U.S. patent application Ser. No. 15/603,560, filed on May 24, 2017, which is s a 35 § U.S.C. 111(a) continuation application which claims the benefit of priority to PCT/US2015/062141, filed on Nov. 23, 2015, which claims priority to U.S. Provisional Application, 62/083,691, filed on Nov. 24, 2014. The entire contents of each of the foregoing applications are incorporated herein by reference.

This application is related to PCT Application Nos. PCT/US2012/065601, filed on Nov. 16, 2012, PCT/US2014/039149, filed on May 22, 2014, U.S. patent application Ser. No. 14/947,025, filed on Nov. 20, 2015, U.S. patent application Ser. No. 15/695,254, filed on Sep. 5, 2017, U.S. patent application Ser. No. 16/191,579, filed on Nov. 15, 2018, The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on Jan. 24, 2019, is named 121301_02903_SL.txt and is 48,919 bytes in size.

BACKGROUND OF THE INVENTION

TMPRSS6 (Transmembrane Protease, Serine 6) gene encodes TMPRSS6, also known as matriptase-2, a type II serine protease. It is primarily expressed in the liver, although high levels of TMPRSS6 mRNA are also found in the kidney, with lower levels in the uterus and much smaller amounts detected in many other tissues (Ramsay et al., Haematologica (2009), 94(6), 840-849). TMPRSS6 plays a role in iron homeostatis by binding and proteolytically degrading the hepcidin activator and BMP co-receptor HJV (hemojuvelin), which causes down-regulation of hepcidin levels.

TMPRSS6 consists of a short N-terminal intracytoplasmic tail, a type II transmembrane domain, a stem region composed of two extracellular CUB (complement factor Cls/Clr, urchin embryonic growth factor and BMP (bone morphogenetic protein)) domains, three LDLR (low-density-lipoprotein receptor class A) domains, and a C-terminal trypsin-like serine protease domain. There are also consensus sites for N-glycosylation in the extracellular domain, and a potential phosphorylation site in the intracytoplasmic tail region.

Numerous disorders can be associated with iron overload, a condition characterized by increased levels of iron. Iron overload can result in excess iron deposition in various tissues and can lead to tissue and organ damage. Accordingly, methods for effective treatment of disorders associated with iron overload are currently needed.

SUMMARY OF THE INVENTION

The present invention provides compositions comprising RNAi agents, e.g., double-stranded iRNA agents, targeting TMPRSS6. The present invention also provides methods using the compositions of the invention for inhibiting TMPRSS6 expression and for treating TMPRSS6 associated disorders, e.g., iron overload associated disorders, such as thalassemia, e.g., β-thalassemia, or hemochromatosis.

Accordingly, in one aspect, the present invention provides RNAi agents, e.g., double-stranded RNAi agents, capable of inhibiting the expression of TMPRSS6 (matriptase-2) in a cell, wherein the double stranded RNAi agent comprises a sense strand and an antisense strand forming a duplex, wherein the sense strand and the antisense strand comprise the sense and antisense strand nucleotide sequences of any one of the duplexes provided in any one of Tables 6, 7, and 8. In one embodiment, the sense strand and the antisense strand comprise the sense and antisense strand nucleotide sequences of a duplex selected from the group consisting of AD-63202, AD-64372, AD-64373, AD-64374, AD-64375, AD-64376, AD-64377, AD-64378, AD-64380, AD-64381, AD-64382, AD-64384, AD-64385, AD-64386, AD-64387, AD-64389, AD-64601, AD-64569, AD-64604, AD-64567, AD-60940, AD-64601, AD-65105, AD-65106, AD-65107, AD-65108, AD-65109, AD-65110, AD-65111, AD-65112, AD-61002, AD-66014, AD-66015, and AD-65189.

In certain embodiments, the sense strand and the antisense strand comprise the sense and antisense strand nucleotide sequences of a duplex selected from the group consisting of AD-63202, AD-64372, AD-64373, AD-64375, AD-64376, AD-64377, AD-64378, AD-64380, AD-64381, AD-64382, AD-64384, AD-64385, AD-64386, AD-64387, AD-64389, AD-64569, AD-64604, AD-60940, AD-65105, AD-65106, AD-65107, AD-65108, AD-65109, AD-65111, AD-66014, and AD-65189.

In certain embodiments, the sense strand and the antisense strand comprise the sense and antisense strand nucleotide sequences of a duplex selected from the group consisting of AD-64376, AD-64377, AD-64378, AD-64382, AD-64386, AD-64387, AD-64389, AD-65105, AD-65111, AD-66014, and AD-65189.

In certain embodiments, the sense strand and the antisense strand comprise the sense and antisense strand nucleotide sequences of a duplex selected from the group consisting of AD-64377, AD-65105, AD-61002, AD-66014, and AD-65189.

In one embodiment, double-stranded RNAi agent is further conjugated to a ligand. In one embodiment, the ligand is one or more GalNAc derivatives attached through a bivalent or trivalent branched linker. In another embodiment, the ligand is

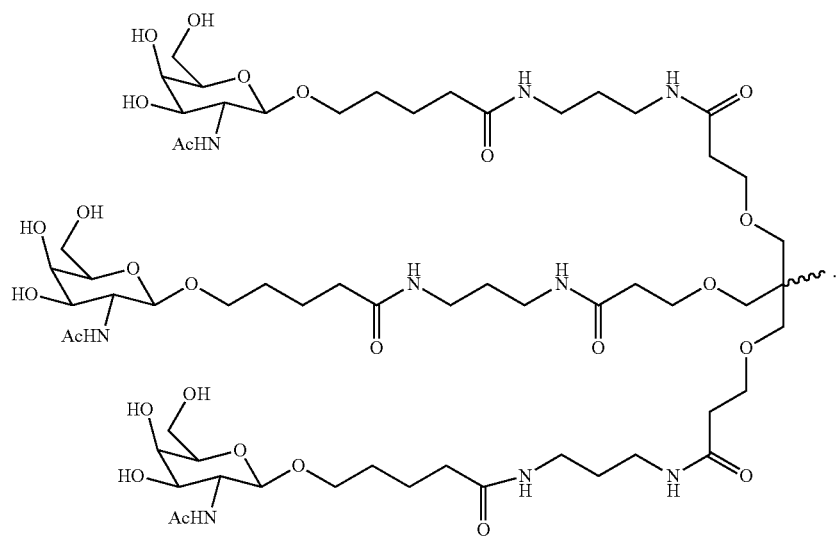 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the ligand is attached to the 3' end of the sense strand.

In one embodiment, the RNAi agent is conjugated to the ligand as shown in the following schematic taining the cell produced in step (a) for a time sufficient to obtain degradation of the mRNA transcript of a TMPRSS6 gene, thereby inhibiting expression of the TMPRSS6 gene in the cell.

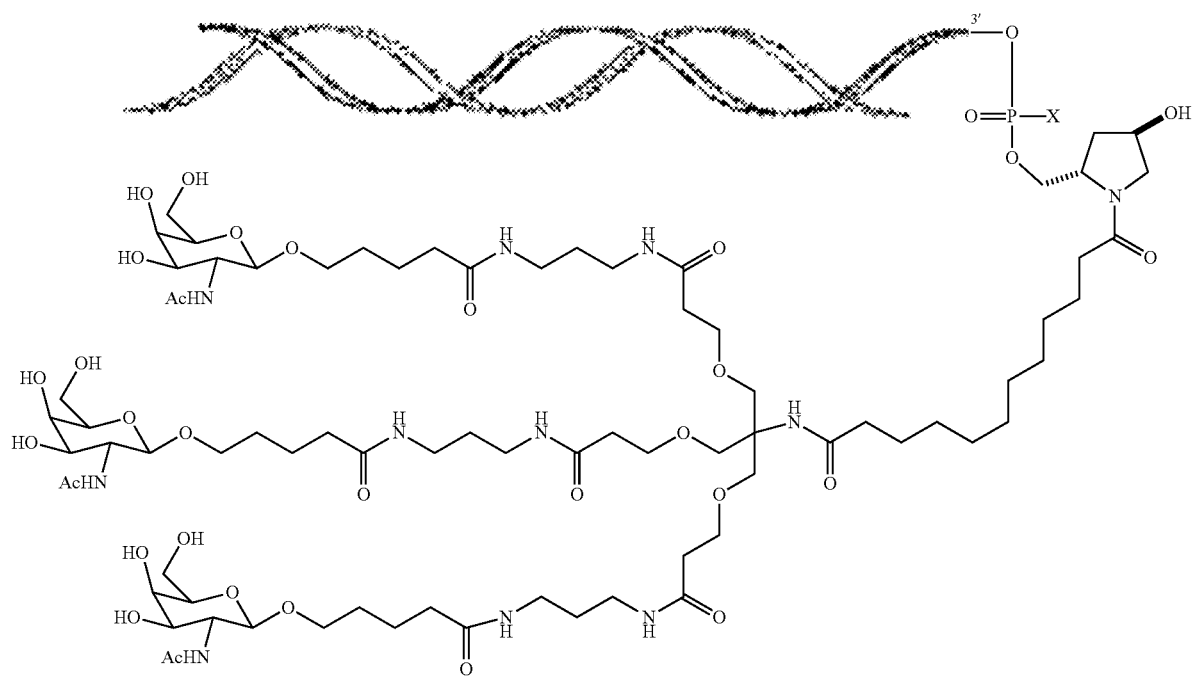

wherein X is O or S. In a specific embodiment, X is O.

The present invention also provides vectors, cells comprising such vectors, and pharmaceutical compositions comprising the double stranded RNAi agents of the invention.

In one aspect, the present invention provides methods of inhibiting TMPRSS6 expression in a cell. The methods include contacting the cell with an RNAi agent, e.g., a double stranded RNAi agent, or a vector of the invention or a pharmaceutical composition of the invention; and main- In one embodiment, the cell is within a subject.

In one embodiment, the subject is a human.

In one embodiment, the TMPRSS6 expression is inhibited by at least about 30%, 35%, 40%, 45%, 50%, 55%, 60%, 65%, 70%, 75%, 80%, 85%, 90%, 95%, 98%, or 100%.

In another embodiment, hepcidin gene expression is increased in the subject by at least about 10%.

In one embodiment, serum iron concentration is decreased in the subject to a normal level, e.g., decreased by at least about 20%.

In another embodiment, a percent transferrin saturation is decreased in the subject to a normal level, e.g., decreased by at least about 20%.

In another aspect, the present invention provides methods of treating a subject having a disorder mediated by, or associated with, TMPRSS6 expression. The methods include administering to the subject a therapeutically effective amount of an RNAi agent, e.g., a double stranded RNAi agent or a vector of the invention or a pharmaceutical composition of the invention, thereby treating the subject.

In one embodiment, the subject is a human.

In one embodiment, the subject has a disorder associated with iron overload, e.g., hereditary hemochromatosis, β-thalassemia (e.g., β-thalassemia major and β-thalassemia intermedia) erythropoietic porphyria, Parkinson's Disease, Alzheimer's Disease, or Friedreich's Ataxia.

In one embodiment, the RNAi agent, e.g., double stranded RNAi agent, is administered at a dose of about 0.01 mg/kg to about 30 mg/kg In one embodiment, the RNAi agent, e.g., double stranded RNAi agent, is administered subcutaneously or intravenously.

In one embodiment, the RNAi agent is administered in two or more doses.

In yet another aspect, the present invention provides methods of treating an iron overload associated disorder in a subject. The methods include administering to the subject a therapeutically effective amount of an RNAi agent, e.g., a double stranded RNAi agent, thereby treating the subject.

In one embodiment, the iron overload associated disorder is hemochromatosis. In another embodiment, the iron overload associated disorder is a thalassemia, e.g., β-thalassemia (e.g., β-thalassemia major and β-thalassemia intermiedia), or erythropoietic porphyria. In yet another embodiment, the iron overload associated disorder is a neurological disease, e.g., Parkinson's Diasease, Alzheimer's Disease, or Friedreich's Ataxia.

In one embodiment, the subject is a primate or rodent. In another embodiment, the subject is a human.

In one embodiment, administering results in a decrease in iron level, ferritin level, and/or transferrin saturation level in the subject.

In one embodiment, the methods further comprise determining the iron level, ferritin level, and/or ferritin saturation level in the subject.

In one embodiment, the methods of the invention which include administering an iRNA agent of the invention (or pharmaceutical composition of the invention) to a subject are practiced in combination with administration of additional pharmaceuticals and/or other therapeutic methods. In one embodiment, the methods of the invention further comprise administering an iron chelator, e.g., deferiprone, deferoxamine, and deferasirox, to a subject.

The present invention is further illustrated by the following detailed description and drawings.

BRIEF DESCRIPTION OF THE DRAWINGS

FIG. 8A is a graph depicting the relative levels of TMPRSS6 mRNA in the liver of C57BL/6 mice on the indicated days following administration of a single subcutaneous dose at the indicated concentration of the indicated iRNA agents of the same sequence with different chemistries The points represent the mean from three mice at each time point and the error bars represent the standard deviation of the mean.

FIG. 8B is a graph depicting the relative levels of transferrin saturation in the liver of C57BL/6 mice on the indicated days following administration of a single subcutaneous dose at the indicated concentration of the indicated iRNA agents having the same sequence with different chemistry or PBS (control). The points represent the mean from three mice at each time point and the error bars represent the standard deviation of the mean.

DETAILED DESCRIPTION OF THE INVENTION

Figure 1:
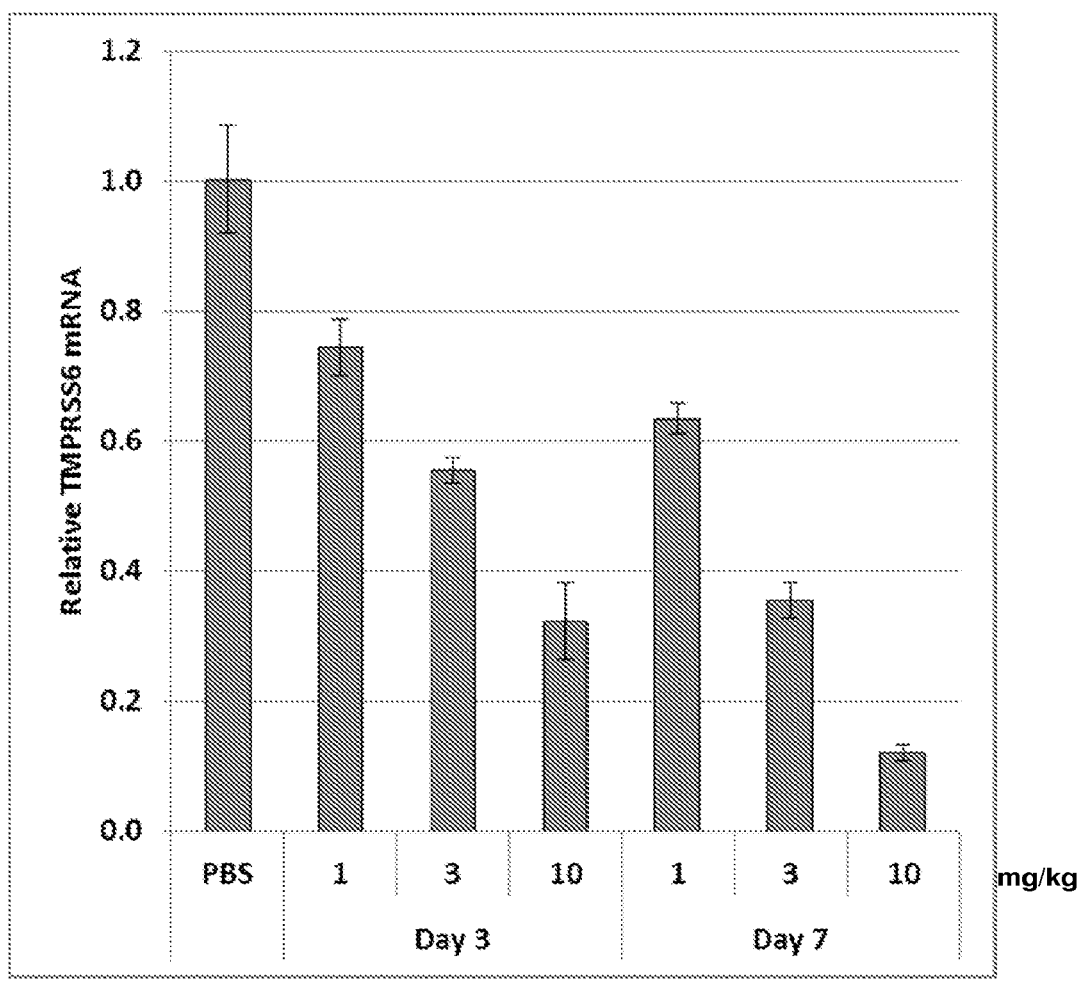
FIG. 1 is a graph showing relative levels of TMPRSS6 mRNA in the liver of wild-type mice following administration of a single dose of 1 mg/kg, 3 mg/kg, or 10 mg/kg of the iRNA agent AD-59743.

The present invention provides compositions comprising RNAi agents, e.g., double-stranded iRNA agents, targeting TMPRSS6. The present invention also provides methods using the compositions of the invention for inhibiting TMPRSS6 expression and for treating TMPRSS6 associated disorders, e.g., β-thalassemia or hemochromatosis.

TMPRSS6 plays an important role in iron homeostasis as an inhibitor of HAMP gene expression. The HAMP gene encodes the liver hormone hepcidin, which is a central regulator of iron homeostasis. Hepcidin binds to the iron exporter protein ferroportin (FPN1), which is localized mainly on absorptive enterocytes, hepatocytes and macrophages. Hepcidin binding to the extracellular domain of ferroportin leads to the internalization and degradation of ferroportin, thus decreasing the absorption of dietary iron from the intestine, and the release of iron from macrophages and hepatocytes. HAMP gene expression can be stimulated in response to iron through Bone Morphogenetic Protein (BMP)/Sons of Mothers Against Decapentaplegic (SMAD)-dependent signal transduction cascade mediated by the BMP-co-receptor hemojuvelin (HJV). The key role of TMPRSS6 in HAMP regulation is in the inhibition of BMP-mediated HAMP upregulation. TMPRSS6 inhibits BMP-mediated HAMP upregulation by cleaving the BMP co-receptor HJV, which is essential for BMP-mediated HAMP upregulation; thus preventing BMP signaling, SMAD translocation to the nucleus, and HAMP transcriptional activation.

Several human and mouse studies have confirmed the role of TMPRSS6 in HAMP regulation and iron homeostasis (Du et al. *Science* 2008, Vol. 320, pp 1088-1092; Folgueras et al. *Blood* 2008, Vol. 112, pp 2539-45). Studies have shown that loss of function mutations in TMPRSS6 can lead to the upregulation of hepcidin expression, causing an inherited iron deficiency anemia called iron refractory iron deficiency anemia (IRIDA) (Finberg. Seminars in *Hematology* 2009, Vol. 46, pp 378-86), which is characterized by elevated hepcidin levels, hypochromic microcytic anemia, low mean corpuscular volume (MCV), low transferrin saturation, poor absorption of oral iron, and incomplete response to parenteral iron. However, loss of function mutations in positive regulators of HAMP (e.g., BMP1, BMP4, and HFE) have been shown to downregulate hepcidin expression and cause iron overload disorders (Milet et al. *Am J Hum Gen* 2007, Vol. 81, pp 799-807; Finberg et al. *Blood* 2011, Vol. 117, pp 4590-9). In the primary iron overload disorders, collectively called hereditary hemochromatosis (HH), in anemias characterized by massive ineffective hematopoiesis, and in iron overload (secondary hemochromatosis), such as β-thalassemia *intermedia* (TI), hepcidin levels are low despite elevated serum iron concentrations and iron stores. A mouse model of β-thalassemia *intermedia* has demonstrated that the loss of TMPRSS6 expression leads to elevated levels of hepcidin (Finberg et al., *Blood,* 2010, Vol. 117, pp 4590-4599).

The present invention describes iRNA agents, compositions and methods for modulating the expression of a TMPRSS6 gene. In certain embodiments, expression of TMPRSS6 is reduced or inhibited using a TMPRSS6-specific iRNA agent, thereby leading to increase HAMP expression, and decreased serum iron levels. Thus, inhibition of TMPRSS6 gene expression or activity using the iRNA compositions featured in the invention can be a useful approach to therapies aimed at reducing the iron levels in a subject. Such inhibition can be useful for treating iron overload associated disorders, such as hemochromatosis or thalassemia, e.g., β-thalassemia (e.g., β-thalassemia major and β-thalassemia intermiedia).

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "TMPRSS6" refers to the type II plasma membrane serine protease (TTSP) gene or protein. TMPRSS6 is also known as matriptase-2, IRIDA (iron refractory iron-deficiency anemia), transmembrane protease serine 6, type II transmembrane serine protease 6, and membrane-bound mosaic serine proteinase matriptase-2. TMPRSS6 is a serine protease Type II transmembrane protein of approximately 899 amino acids in length. TMPRSS6 contains multiple domains, e.g., a short endo domain, a transmembrane domain, a sea urchin sperm protein/enteropeptidase domain/agrin (SEA) domain, two complement factor/urchin embryonic growth factor/BMP domains (CUB), three LDL-R class a domains (LDLa), and a trypsin-like serine protease domain with conserved His-Asp-Ser triad (HDS). The term "TMPRSS6" includes human TMPRSS6, the amino acid and nucleotide sequence of which may be found in, for example, GenBank Accession No. GI:56682967 (SEQ ID NO: 1); mouse TMPRSS6, the amino acid and nucleotide sequence of which may be found in, for example, GenBank Accession No. GI:125656151; rat TMPRSS6, the amino acid and nucleotide sequence of which may be found in, for example, GenBank Accession No. GI:194474097; rhesus TMPRSS6, the amino acid and nucleotide sequence of which may be found in, for example, GenBank Accession No. XM_001085203.2 (GI:297260989) and XM_001085319.1 (GI:109094061). Additional examples of AGT mRNA sequences are readily available using publicly available databases, e.g., GenBank, UniProt, OMIM, and the *Macaca* genome project web site.

The term"TMPRSS6," as used herein, also refers to naturally occurring DNA sequence variations of the TMPRSS6 gene, such as a single nucleotide polymorphism (SNP) in the TMPRSS6 gene. Exemplary SNPs may be found in the dbSNP database available at www.ncbi.nlm nih.gov/projects/SNP.

As used herein, "target sequence" refers to a contiguous portion of the nucleotide sequence of an mRNA molecule formed during the transcription of a TMPRSS6 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine, 2'-deoxythymidine or thymidine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of TMPRSS6 in a cell, e.g., a cell within a subject, such as a mammalian subject.

In one embodiment, an RNAi agent of the invention includes a single stranded RNA that interacts with a target RNA sequence, e.g., a TMPRSS6 target mRNA sequence, to direct the cleavage of the target RNA. Without wishing to be bound by theory, it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a TMPRSS6 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In yet another embodiment, the present invention provides single-stranded antisense oligonucleotide molecules targeting TMPRSS6. A "single-stranded antisense oligonucleotide molecule" is complementary to a sequence within the target mRNA (i.e., TMPRSS6). Single-stranded antisense oligonucleotide molecules can inhibit translation in a stoichiometric manner by base pairing to the mRNA and physically obstructing the translation machinery, see Dias, N. et al., (2002) *Mol Cancer Ther* 1:347-355. Alternatively, the single-stranded antisense oligonucleotide molecules inhibit a target mRNA by hydridizing to the target and cleaving the target through an RNaseH cleavage event. The single-stranded antisense oligonucleotide molecule may be about 10 to about 30 nucleotides in length and have a sequence that is complementary to a target sequence. For example, the single-stranded antisense oligonucleotide molecule may comprise a sequence that is at least about 10, 11, 12, 13, 14, 15, 16, 17, 18, 19, 20, or more contiguous nucleotides from any one of the antisense nucleotide sequences described herein, e.g., the sequences provided in any one of Tables 1, 2, 4, and 6-8, or bind any of the target sites described herein. The single-stranded antisense oligonucleotide molecules may comprise modified RNA, DNA, or a combination thereof.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a TMPRSS6 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/ or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs.

In one embodiment, an RNAi agent of the invention is a dsRNA of 24-30 nucleotides that interacts with a target RNA sequence, e.g., a TMPRSS6 target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). As used herein, a "nucleotide overhang" refers to the unpaired nucleotide or nucleotides that protrude from the duplex structure of an RNAi agent when a 3'-end of one strand of the RNAi agent extends beyond the 5'-end of the other strand, or vice versa. "Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" refers to the strand of a double stranded RNAi agent which includes a region that is substantially complementary to a target sequence (e.g., a human TMPRSS6 mRNA). As used herein, the term "region complementary to part of an mRNA encoding TMPRSS6" refers to a region on the antisense strand that is substantially complementary to part of a TMPRSS6 mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12, and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. For example, a complementary sequence is sufficient to allow the relevant function of the nucleic acid to proceed, e.g., RNAi. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3, or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary," and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding TMPRSS6) including a 5' UTR, an open reading frame (ORF), or a 3' UTR. For example, a polynucleotide is complementary to at least a part of a TMPRSS6 mRNA if the sequence is substantially complementary to a non-interrupted portion of an mRNA encoding TMPRSS6.

The term "inhibiting," as used herein, is used interchangeably with "reducing," "silencing," "downregulating," "suppressing," and other similar terms, and includes any level of inhibition.

The phrase "inhibiting expression of a TMPRSS6," as used herein, includes inhibition of expression of any TMPRSS6 gene (such as, e.g., a mouse TMPRSS6 gene, a rat TMPRSS6 gene, a monkey TMPRSS6 gene, or a human TMPRSS6 gene) as well as variants, (e.g., naturally occurring variants), or mutants of a TMPRSS6 gene. Thus, the TMPRSS6 gene may be a wild-type TMPRSS6 gene, a mutant TMPRSS6 gene, or a transgenic TMPRSS6 gene in the context of a genetically manipulated cell, group of cells, or organism.

"Inhibiting expression of a TMPRSS6 gene" includes any level of inhibition of a TMPRSS6 gene, e.g., at least partial suppression of the expression of a TMPRSS6 gene, such as an inhibition of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

The expression of a TMPRSS6 gene may be assessed based on the level of any variable associated with TMPRSS6 gene expression, e.g., TMPRSS6 mRNA level, TMPRSS6 protein level, hepcidin mRNA level, hepcidin protein level, transferrin saturation level, or iron levels in tissues or serum. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control), and known population levels.

The phrase "contacting a cell with a double stranded RNAi agent," as used herein, includes contacting a cell by any possible means. Contacting a cell with a double stranded RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, the bloodstream or the subcutaneous space, such that the agent will subsequently reach the tissue where the cell to be contacted is located. For example, the RNAi agent may contain and/or be coupled to a ligand, e.g., a GalNAc3 ligand, that directs the RNAi agent to a site of interest, e.g., the liver. Combinations of in vitro and in vivo methods of contacting are also possible. In connection with the methods of the invention, a cell might also be contacted in vitro with an RNAi agent and subsequently transplanted into a subject.

A "patient" or "subject," as used herein, is intended to include either a human or non-human animal, preferably a mammal, e.g., human or a monkey. Most preferably, the subject or patient is a human.

A "TMPRSS6 associated disorder", as used herein, is intended to include any disorder that can be treated or prevented, or the symptoms of which can be alleviated, by inhibiting the expression of TMPRSS6. In some embodiments, the TMPRSS6 associated disorder is also associated with iron overload, a condition characterized by elevated iron levels, or iron dysregulation. Iron overload may be caused, for example, by hereditary conditions, by elevated iron uptake from diet, or by excess iron administered parenterally that includes intravenous injection of excess iron, and transfusional iron overload.

TMPRSS6 associated disorders include, but are not limited to, hereditary hemochromatosis, idiopathic hemochromatosis, primary hemochromatosis, secondary hemochromatosis, severe juvenile hemochromatosis, neonatal hemochromatosis, sideroblastic anemia, hemolytic anemia, dyserythropoietic anemia, sickle-cell anemia, hemoglobinopathy, thalassemia (e.g., β-thalassemia and α-thalassemia), chronic liver diseases, porphyria cutanea tarda, erythropoietic porphyria, atransferrinemia, hereditary tyrosinemia, cerebrohepatorenal syndrome, idiopathic pulmonary hemosiderosis, and renal hemosiderosis.

TMPRSS6 associated disorders include disorders associated with oral administration of excess iron, transfusional iron overload, and intravenous injection of excess iron.

TMPRSS6 associated disorders also include disorders with symptoms that are associated with or may be caused by iron overload. Such symptoms include increased risk for liver disease (cirrhosis, cancer), heart attack or heart failure, diabetes mellitus, osteoarthritis, osteoporosis, metabolic syndrome, hypothyroidism, hypogonadism, and, in some cases, premature death. In one embodiment, TMPRSS6 associated disorders include neurodegenerative disorders associated with iron overload and/or iron dysregulation, such as Alzheimer's Disease, Parkinson's Disease, Huntington's Disease, Friedreich's Ataxia, epilepsy, and multiple sclerosis. Administration of an iRNA that targets TMPRSS6, e.g., an iRNA described in any one of Tables 4 and 6-8 can treat one or more of these symptoms, or prevent the development or progression of a disease or disorder that is aggravated by increased iron levels.

In one embodiment, a TMPRSS6 associated disorder is a β-thalassemia. A (3-thalassemia is any one of a group of hereditary disorders characterized by a genetic deficiency in the synthesis of beta-globin chains. In the homozygous state, beta thalassemia ("thalassemia major") causes severe, transfusion-dependent anemia. In the heterozygous state, the beta thalassemia trait ("thalassemia minor") causes mild to moderate microcytic anemia.

"Thalassemia intermedia" is a β-thalassemia that results in subjects in whom the clinical severity of the disease is somewhere between the mild symptoms of β-thalassemia minor and the β-thalassemia major. The diagnosis is a clinical one that is based on the patient maintaining a satisfactory hemoglobin (Hb) level of at least 6-7 g/dL at the time of diagnosis without the need for regular blood transfusions.

In one embodiment, a β-thalassemia is thalassemia major. In another embodiment, a β-thalassemia is thalassemia *intermedia*.

"Therapeutically effective amount," as used herein, is intended to include the amount of an RNAi agent that, when administered to a patient for treating a TMPRSS6 associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by TMPRSS6 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of a TMPRSS6-associated disease, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. RNAi gents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue (or subcomponents thereof) derived from the subject.

II. iRNAs of the Invention

Described herein are improved double-stranded RNAi agents which inhibit the expression of a TMPRSS6 gene in a cell, such as a cell within a subject, e.g., a mammal, such as a human having a TMPRSS6 associated disorder, e.g., β-thalassemia (e.g., β-thalassemia major and β-thalassemia intermiedia) or hemochromatosis, and uses of such double-stranded RNAi agents.

Accordingly, the invention provides double-stranded RNAi agents with chemical modifications capable of inhibiting the expression of a target gene (i.e., a TMPRSS6 gene) in vivo.

The sense strand and antisense strand typically form a duplex double stranded RNA ("dsRNA"), also referred to herein as an "RNAi agent."

Any of the nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; 5,625,050; 6,028,188; 6,124,445; 6,160, 109; 6,169,170; 6,172,209; 6,239,265; 6,277,603; 6,326, 199; 6,346,614; 6,444,423; 6,531,590; 6,534,639; 6,608, 035; 6,683,167; 6,858,715; 6,867,294; 6,878,805; 7,015, 315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S-, or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$.

Other modifications include 2'-methoxy (2'-$OCH_3$), 2'-aminopropoxy (2'-$OCH_2CH_2CH_2NH_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Modified nucleobases are present in glycol nucleic acids e.g., GNAs, e.g., thymidine-glycol nucleic acid, e.g., the S-isomer, cytidine-glycol nucleic acid, and adenosine-glycol nucleic acid (GNA) (see, e.g., US 20110306653). Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6, and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT(idT), and others. Disclosure of this modification can be found in PCT Publication No. WO 2011/005861.

A. Ligands

The double-stranded RNA (dsRNA) agents of the invention may optionally be conjugated to one or more ligands. The ligand can be attached to the sense strand, antisense strand, or both strands, at the 3'-end, 5'-end, or both ends. For instance, the ligand may be conjugated to the sense strand. In preferred embodiments, the ligand is conjugated to the 3'-end of the sense strand. In one preferred embodiment, the ligand is a GalNAc ligand. In particularly preferred embodiments, the ligand is $GalNAc_3$:

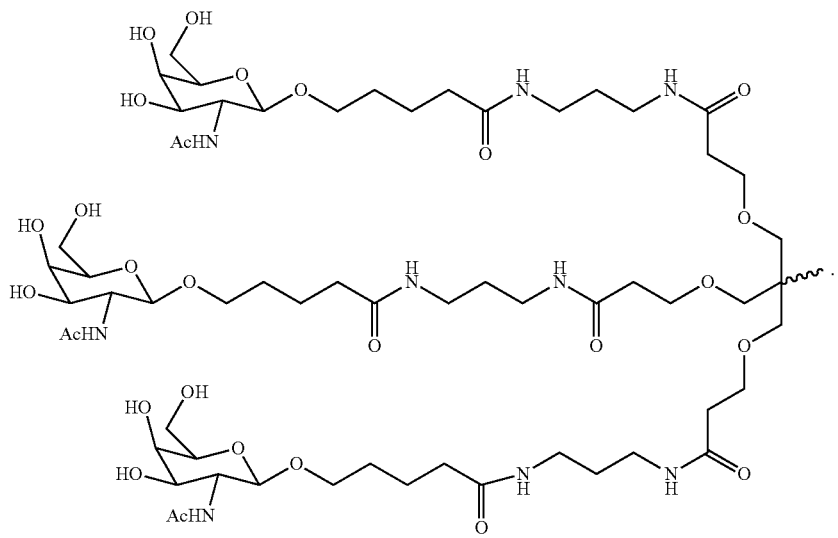 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the ligand, e.g., GalNAc ligand, is attached to the 3' end of the RNAi agent. In one embodiment, the RNAi agent is conjugated to the ligand, e.g., GalNAc ligand, as shown in the following schematic cellular or organ compartment, tissue, organ or region of the body, as, e.g., compared to a species absent such a ligand. Ligands providing enhanced affinity for a selected target are also termed targeting ligands.

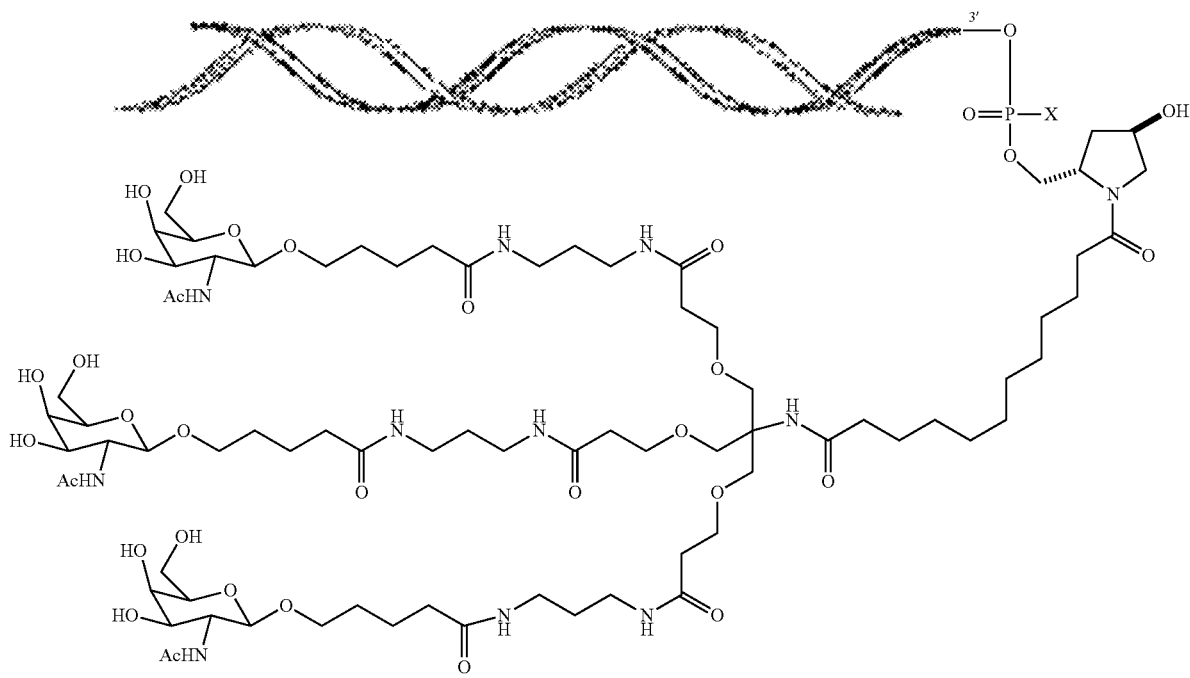

wherein X is O or S. In one embodiment, X is O.

A wide variety of entities can be coupled to the RNAi agents of the present invention. Preferred moieties are ligands, which are coupled, preferably covalently, either directly or indirectly via an intervening tether.

In preferred embodiments, a ligand alters the distribution, targeting or lifetime (e.g., half life) of the molecule into which it is incorporated. In preferred embodiments a ligand provides an enhanced affinity for a selected target, e.g., molecule, cell or cell type, compartment, receptor e.g., a Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., *Biochemistry*, 1987, 26: 2964-2972), the EALA peptide (Vogel et al., *J. Am. Chem. Soc.*, 1996, 118: 1581-1586), and their derivatives (Turk et al., *Biochem. Biophys. Acta*, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (RMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid, or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g., acridines), cross-linkers (e.g., psoralen, mitomycin C), porphyrins (TPPC4, texaphyrin, Sapphyrin), polycyclic aromatic hydrocarbons (e.g., phenazine, dihydrophenazine), artificial endonucleases or a chelator (e.g., EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by, for example, activating an inflammatory response. Exemplary ligands that would have such an effect include tumor necrosis factor alpha (TNF-alpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell.

These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal, or other vitamins or nutrients taken up by cancer cells. Also included are HSA, low density lipoprotein (LDL), and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 2). An RFGF analogue (e g, amino acid sequence AALLPVLLAAP (SEQ ID NO: 3)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) (SEQ ID NO: 4) and the *Drosophila* Antennapedia protein (RQIKI-WFQNRRMKWKK) (SEQ ID NO: 5) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature*, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., *Cancer Res.*, 62:5139-43, 2002). An RGD peptide can facilitate targeting of an iRNA agent to tumors of a variety of other tissues, including the lung, kidney, spleen, or liver (Aoki et al., *Cancer Gene Therapy* 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., *Jour. Nucl. Med.*, 42:326-336, 2001). Peptides that target markers enriched in proliferating cells can be used. For example, RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type of ligand target PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H$_2$A peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL, and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polycations, masked oligo or poly cations or anions, acetals, polyacetals, ketals/polyketyals, orthoesters, polymers with masked or unmasked cationic or anionic charges, or dendrimers with masked or unmasked cationic or anionic charges.

PK modulator stands for pharmacokinetic modulator. PK modulators include lipophiles, bile acids, steroids, phospholipid analogues, peptides, protein binding agents, PEG, vitamins etc. Examplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin, etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple phosphorothioate linkages in the backbone are also amenable to the present invention as ligands (e.g., as PK modulating ligands).

In addition, aptamers that bind serum components (e.g., serum proteins) are also amenable to the present invention as PK modulating ligands.

Other ligand conjugates amenable to the invention are described in U.S. Patent Publication Nos. US20050107325, US20050164235, US20060008822, US2008010880, and US20080255345, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g., a carrier described herein. The ligand or tethered ligand may be present on a monomer when the monomer is incorporated into the growing strand. In some embodiments, the ligand may be incorporated via coupling to a "precursor" monomer after the "precursor" monomer has been incorporated into the growing strand. For example, a monomer having, e.g., an amino-terminated tether (i.e., having no associated ligand), e.g., TAP—$(CH_2)_n$—$NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated, e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a bivalent or trivalent branched linker.

In one embodiment, the dsRNA of the invention is conjugated to a bivalent and trivalent branched linkers include the structures shown in any of formula (IV)-(VII):

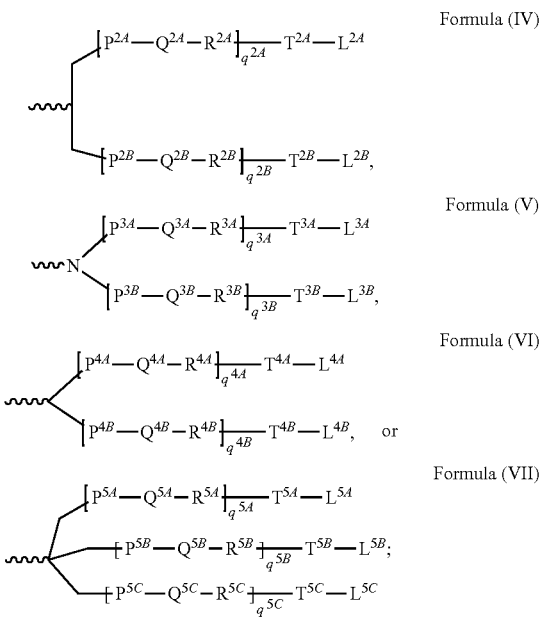

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different; $P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R"), CC or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—O,

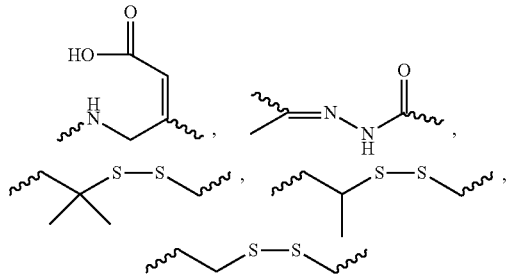

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and R$^a$ is H or amino acid side chain.

Trivalent conjugating GalNAc derivatives are particularly useful for use with RNAi agents for inhibiting the expression of a target gene, such as those of formula (VII):

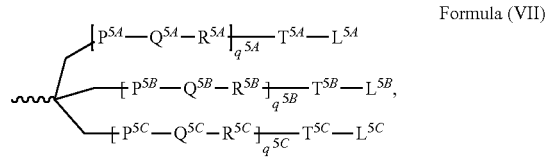

Formula (VII)

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the following compounds:

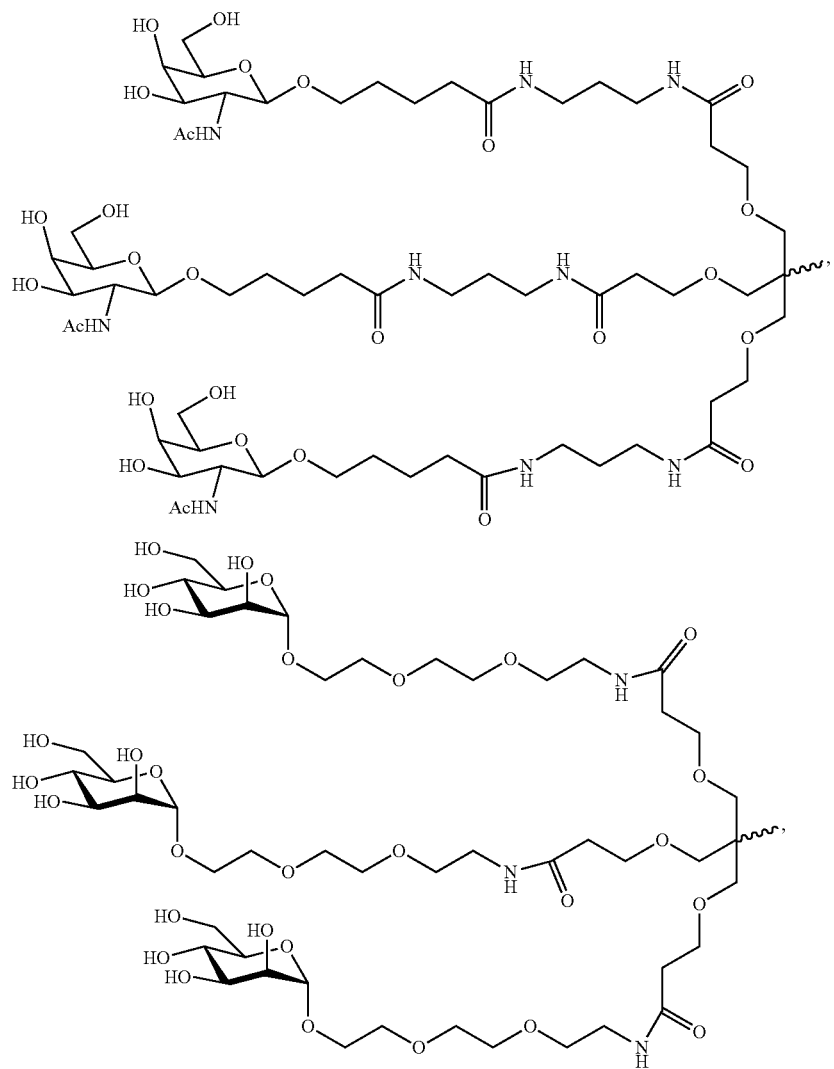

-continued
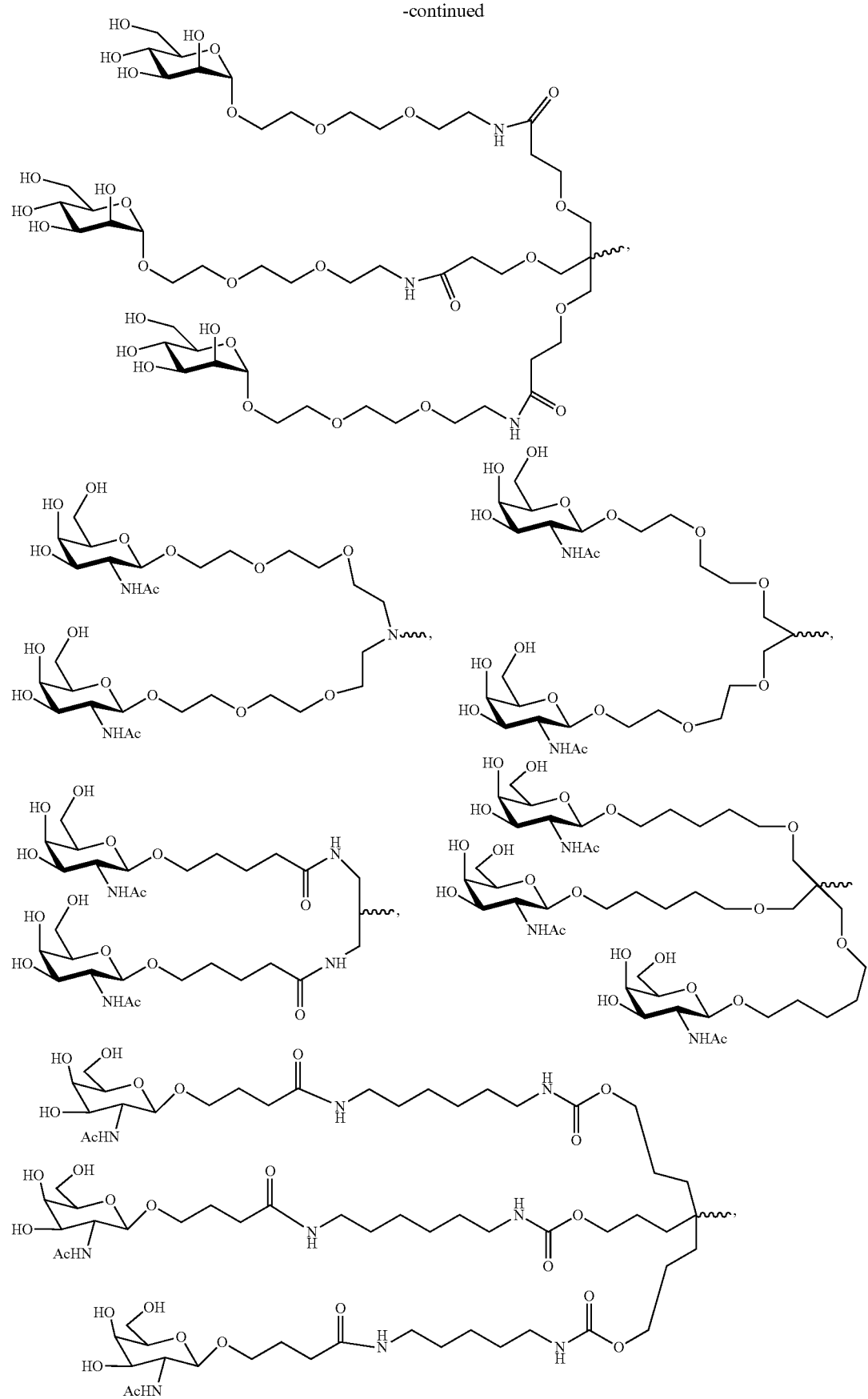

-continued

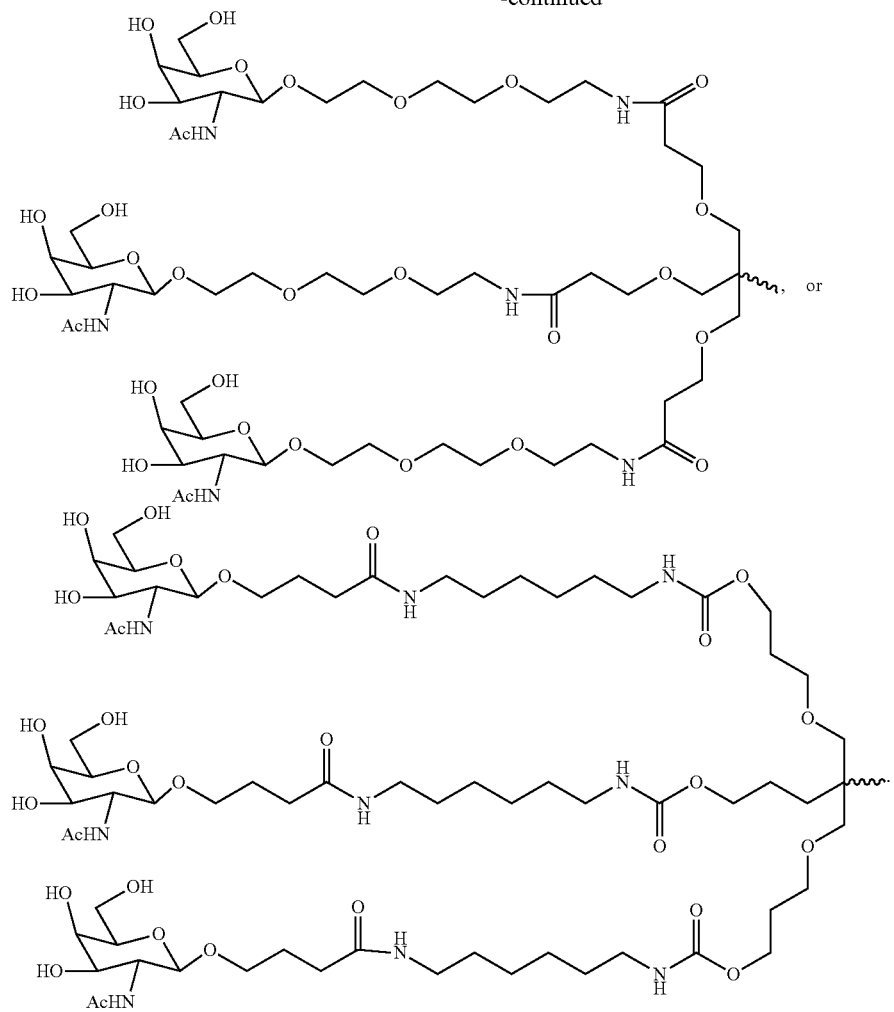

In other embodiments, the RNAi agent for use in the methods of the invention is AD-59743.

III. Delivery of an iRNA of the Invention

The delivery of an iRNA agent of the invention to a cell e.g., a cell within a subject, such as a human subject (e.g., a subject in need thereof, such as a subject having a TMPRSS6 associated disorder, such as a hemochromatosis) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) J. Biomed. Biotechnol. 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

IV. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a TMPRSS6 associated disease or disorder, e.g. hemochromatosis. Such pharmaceutical compositions are formulated based on the mode of delivery. One example is compositions that are formulated for systemic administration via parenteral delivery, e.g., by intravenous (IV) delivery or subcutaneous (SC) delivery. In the methods of the invention, the RNAi agent may be administered in a solution, preferably a sterile solution. Solutions for administration of agents by injection are known in the art.

The pharmaceutical compositions of the invention may be administered in dosages sufficient to inhibit expression of a TMPRSS6 gene.

In general, a suitable dose of an iRNA of the invention will be in the range of about 0.001 to about 200.0 milligrams per kilogram body weight of the recipient per day.

V. Methods for Inhibiting TMPRSS6 Expression

The present invention provides methods of inhibiting expression of TMPRSS6 (matriptase-2) in a cell. The methods include contacting a cell with an RNAi agent, e.g., a double stranded RNAi agent, in an amount effective to inhibit expression of the TMPRSS6 in the cell, thereby inhibiting expression of the TMPRSS6 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a TMPRSS6" is intended to refer to inhibition of expression of any TMPRSS6 gene (such as, e.g., a mouse TMPRSS6 gene, a rat TMPRSS6 gene, a monkey TMPRSS6 gene, or a human TMPRSS6 gene) as well as variants or mutants of a TMPRSS6 gene. Thus, the TMPRSS6 gene may be a wild-type TMPRSS6 gene, a mutant TMPRSS6 gene, or a transgenic TMPRSS6 gene in the context of a genetically manipulated cell, group of cells, or organism.

"Inhibiting expression of a TMPRSS6 gene" includes any level of inhibition of a TMPRSS6 gene, e.g., at least partial suppression of the expression of a TMPRSS6 gene. The expression of the TMPRSS6 gene may be assessed based on the level, or the change in the level, of any variable associated with TMPRSS6 gene expression, e.g., TMPRSS6 mRNA level, TMPRSS6 protein level, or lipid levels. This level may be assessed in an individual cell or in a group of cells, including, for example, a sample derived from a subject.

Inhibition may be assessed by a decrease in an absolute or relative level of one or more variables that are associated with TMPRSS6 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a TMPRSS6 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of a TMPRSS6 gene may be manifested by a reduction of the amount of mRNA expressed by a first cell or group of cells (such cells may be present, for example, in a sample derived from a subject) in which a TMPRSS6 gene is transcribed and which has or have been treated (e.g., by contacting the cell or cells with an RNAi agent of the invention, or by administering an RNAi agent of the invention to a subject in which the cells are or were present) such that the expression of a TMPRSS6 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of a TMPRSS6 gene may be assessed in terms of a reduction of a parameter that is functionally linked to TMPRSS6 gene expression, e.g., TMPRSS6 protein expression, hepcidin gene or protein expression, transferrin saturation, or iron levels in tissues or serum. TMPRSS6 gene silencing may be determined in any cell expressing TMPRSS6, either constitutively or by genomic engineering, and by any assay known in the art. The liver is the major site of TMPRSS6 expression. Other significant sites of expression include the kidneys and the uterus.

Inhibition of the expression of a TMPRSS6 protein may be manifested by a reduction in the level of the TMPRSS6 protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a TMPRSS6 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of TMPRSS6 mRNA that is expressed by a cell or group of cells may be determined using any method known in the art for assessing mRNA expression. In one embodiment, the level of expression of TMPRSS6 in a sample is determined by detecting a transcribed polynucleotide, or portion thereof, e.g., mRNA of the TMPRSS6 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (Pre-Analytix, Switzerland). Typical assay formats utilizing ribonucleic acid hybridization include nuclear run-on assays, RT-PCR, RNase protection assays (Melton et al., *Nuc. Acids Res.* 12:7035), northern blotting, in situ hybridization, and microarray analysis.

In one embodiment, the level of expression of TMPRSS6 is determined using a nucleic acid probe. The term "probe", as used herein, refers to any molecule that is capable of selectively binding to a specific TMPRSS6. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to TMPRSS6 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of TMPRSS6 mRNA.

An alternative method for determining the level of expression of TMPRSS6 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of TMPRSS6 is determined by quantitative fluorogenic RT-PCR (i.e., the TaqMan™ System).

The expression levels of TMPRSS6 mRNA may be monitored using a membrane blot (such as used in hybridization analysis such as northern, Southern, dot, and the like), or microwells, sample tubes, gels, beads or fibers (or any solid support comprising bound nucleic acids). See e.g., U.S. Pat. Nos. 5,770,722, 5,874,219, 5,744,305, 5,677,195 and 5,445,934, which are incorporated herein by reference. The determination of TMPRSS6 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of TMPRSS6 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments of the methods of the invention, the RNAi agent is administered to a subject such that the RNAi agent is delivered to a specific site within the subject. The inhibition of expression of TMPRSS6 may be assessed using measurements of the level or change in the level of TMPRSS6 mRNA or TMPRSS6 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

VI. Methods for Treating or Preventing a TMPRSS6 Associated Disorder

The present invention also provides methods for treating or preventing diseases and conditions that can be modulated by TMPRSS6 gene expression. For example, the compositions described herein can be used to treat any disorder associated with iron overload, e.g., a thalassemia (e.g., β-thalassemia or α-thalassemia), primary hemochromatosis, secondary hemochromatosis, severe juvenile hemochromatosis, erythropoietic porphyria, sideroblastic anemia, hemolytic anemia, dyserythropoietic anemia, or sickle-cell anemia. In one embodiment, a TMPRSS6 iRNA is used to treat a hemoglobinopathy. The TMPRSS6 iRNAs of the invention can also be used to treat elevated levels of iron due to other conditions, such as chronic alcoholism.

In thalassemias, the bone marrow synthesizes insufficient amounts of a hemoglobin chain; this in turn reduces the production of red blood cells and causes anemia. Either the α or the β chain may be affected, but β thalassemias are more common. Newborn babies are healthy because their bodies still produce HbF, which does not have β chains; during the first few months of life, the bone marrow switches to producing HbA, and symptoms start to appear.

β-thalassemias result from mutation with either non-expressing (β°) or low expressing (β+) alleles of the HBB gene, β-thalassemias vary in severity depending on the genotype, and include minor/trait β-thalassemia (β/β° or β/β+), intermedia β-thalassemia (β°/β+), and major β-thalassemia (β°/β° or β"7β+).

Thalassemia intermedia (TI) typically presents with little hemolysis, while major β-thalassemia (TM) is typically accompanied by abundant hemolysis which causes, e.g., anemia and splenomegaly; and highly ineffective erythropoiesis, which causes bone marrow drive (skeletal changes, oteopenia), increased erythropoietin synthesis, hepato-splenomegaly, consumption of haematinics (megablastic anemia), and high uric acid in blood. The iRNAs of the invention, e.g., TMPRSS6 iRNAs, are better suited for treating the iron overload that typically accompanies thalassemia's that are more TI like (e.g., for treating individuals having a β°/β+, β/β° or β/β+ genotype).

Symptoms of β-thalassemias also include, e.g., complication due to therapy, e.g., iron overload, which causes endocrinopathy, liver fibrosis, and cardiac fibrosis. Administration of an iRNA agent that targets TMPRSS6 can be effective to treat one or more of these symptoms.

α-thalassemias result from mutation with either non-expressing (a°) or low expressing (a+) alleles of the HBA1 or HBA2 genes, orthalassemias vary in severity depending on the genotype, and include trait thalassemia (−α/αα), Hb Bart and Hydrops fetalis (a°/a°), a-Thalaseemia minor (−/αα), (−α/−α), and HbH disease (−/−a). Lower a-globin chains are produced, resulting in an excess of β chains in adults and excess γ chains in newborns. The excess β chains form unstable tetramers (called Hemoglobin H or HbH of 4 beta chains), which have abnormal oxygen dissociation curves. Administration of an iRNA agent that targets TMPRSS6 can be effective to treat iron overload in a subject who has an a-thalassemias.

Symptoms of hemochromatosis include, e.g., abdominal pain, joint pain, fatigue, lack of energy, weakness, darkening of the skin (often referred to as "bronzing"), and loss of body hair. Administration of an iRNA agent that targets TMPRSS6 can be effective to treat one or more of these symptoms.

Other symptoms associated with iron overload include increased risk for liver disease (cirrhosis, cancer), heart attack or heart failure, diabetes mellitus, osteoarthritis, osteoporosis, metabolic syndrome, hypothyroidism, hypogonadism, and in some cases premature death. Iron mismanagement resulting in overload can also accelerate such neurodegenerative diseases as Alzheimer's, early-onset Parkinson's, Huntington's, epilepsy, and multiple sclerosis. Administration of an iRNA agent that targets TMPRSS6, e.g., an iRNA described in Tables 4 and 6-8 can treat one or more of these symptoms, or prevent the development or progression of a disease or disorder that is aggravated by increased iron levels.

The methods of the invention further relate to the use of an iRNA agent or a pharmaceutical composition thereof, e.g., for treating a disorder associated with iron overload, in combination with other pharmaceuticals and/or other therapeutic methods, e.g., with known pharmaceuticals and/or known therapeutic methods, such as, for example, those which are currently employed for treating these disorders. For example, in certain embodiments, an iRNA agent targeting TMPRSS6 is administered in combination with, e.g., iron chelators (e.g., desferoxamine), folic acid, a blood transfusion, a phlebotomy, agents to manage ulcers, agents to increase fetal hemoglobin levels (e.g., hydroxyurea), agents to control infection (e.g., antibiotics and antivirals), agents to treat thrombotic state, or a stem cell or bone marrow transplant. A stem cell transplant can utilize stem cells from an umbilical cord, such as from a relative, e.g., a sibling. Exemplary iron chelators include desferoxamine, Deferasirox (Exjade), deferiprone, vitamin E, wheat germ oil, tocophersolan, and indicaxanthin.

The iRNA agent and an additional therapeutic agent can be administered in the same composition, e.g., parenterally, or the additional therapeutic agent can be administered as part of a separate composition or by another method described herein. Administration of the iRNA agent and the additional therapeutic agent can be at the same time, or at different times and, in any order.

Administration of the iRNA agent of the invention can lower iron levels, lower ferritin levels, and/or lower transferrin saturation levels. For example, administration of the dsRNA can lower serum iron levels and/or lower serum ferritin levels. Transferrin saturation levels can be lowered towards or to a normal level. Transferrin saturation is a measure of the amount of iron bound to serum transferrin, and corresponds to the ratio of serum iron and total iron-binding capacity.

Serum iron levels can be lowered towards or to a normal level.

Administration of the iRNA agent of the invention preferably results in lowered iron levels in the blood, and more particularly in the serum, or in one or more tissues of the mammal. In some embodiments, iron levels are lowered towards or to a normal level.

By "lower" in this context is meant a statistically and/or therapeutically significant decrease in such level. Determination of significance is well within the ability of those of skill in the art.

Administration of the iRNA agent of the invention can increase serum hepcidin levels, and/or increase hepcidin gene expression. For example, administration of the dsRNA can increase serum hepcidin by at least about 10%, 25%, or 50%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, the levels of transferrin saturation or serum ferritin can be monitored for efficacy of a given treatment regime.

Iron level tests are typically performed on a sample of a patient's blood. An iron level test measure the amount of iron in the blood serum that is being carried by the proteins transferrin. A TIBC (Total iron-binding capacity) test measures the amount of iron that the blood would carry if the transferrin were fully saturated. Since transferrin is produced by the liver, the TIBC can be used to monitor liver function and nutrition. The transferrin test is a direct measure of transferrin (also called siderophilin) levels in the blood. The saturation level of transferrin can be calculated by dividing the serum iron level by the TIBC. The ferritin test measures the level of a protein in the blood that stores iron for later use by the body.

The iRNA treatments described herein can be used to treat individuals afflicted with a TMPRSS6 associated disorder, e.g., elevated iron levels, as may be indicated by iron levels in serum e.g., iron levels measuring greater than 350 µg/dL or greater than 15 mg/g dry weight.

The iRNA treatments described herein can also be used to treat individuals having elevated iron levels, as may be indicated by elevated ferritin levels in serum, e.g., ferritin levels measuring greater than 300 µg/L.

The iRNA treatments described herein can further be used to treat individuals having elevated iron levels, as may be indicated by elevated transferrin levels in serum, e.g., transferrin levels measuring greater than 400 mg/dL.

The iRNA treatments described herein can also be used to treat individuals having moderately elevated iron levels, as may be indicated by moderately elevated transferrin saturation levels, e.g., saturation levels of at least about 40%. In addition, the treatment described herein may also be used to prevent elevated iron levels in individuals with only minor elevations in transferrin saturation. One of skill in the art can easily monitor the transferrin saturation levels in subjects The iRNA treatments described herein can be used to treat individuals having elevated iron levels, as may be indicated by a TIBC value greater than 400 µg/dL.

A treatment or preventive effect is evident when there is a statistically significant improvement in one or more parameters of disease status, or by a failure to worsen or to develop symptoms where they would otherwise be anticipated. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale.

As used herein, a "subject" includes a human or non-human animal, preferably a vertebrate, and more preferably a mammal A subject may include a transgenic organism. Most preferably, the subject is a human, such as a human suffering from or predisposed to developing a TMPRSS6 associated disorder.

The RNAi agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof. In preferred embodiments, the agents are administered subcutaneously.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of TMPRSS6, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

VII. Kits

The present invention also provides kits for using any of the iRNA agents and/or performing any of the methods of the invention. Such kits include one or more RNAi agent(s) and instructions for use, e.g., instructions for inhibiting expression of a TMPRSS6 in a cell by contacting the cell with the RNAi agent(s) in an amount effective to inhibit expression of the TMPRSS6. The kits may optionally further comprise means for contacting the cell with the RNAi agent (e.g., an injection device), or means for measuring the inhibition of TMPRSS6 (e.g., means for measuring the inhibition of TMPRSS6 mRNA or TTR protein). Such means for measuring the inhibition of TMPRSS6 may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Examples

Materials and Methods

The following materials and methods were used in the Examples.

cDNA Synthesis Using ABI High Capacity cDNA Reverse Transcription Kit (Applied Biosystems, Foster City, Calif., Cat #4368813)

A master mix of 2 µl 10× Buffer, 0.8 µl 25×dNTPs, 2 µl Random primers, Reverse Transcriptase, 1 µl RNase inhibitor and 3.2 µl of H₂O per reaction was added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Cell Culture and Transfections

Hep3B cells (ATCC, Manassas, Va.) were grown to near confluence at 37° C. in an atmosphere of 5% $CO_2$ in EMEM (ATCC) supplemented with 10% FBS, streptomycin, and glutamine (ATCC) before being released from the plate by trypsinization. Transfection was carried out by adding 14.8 µl of Opti-MEM plus 0.4.1 of Lipofectamine RNAiMax per well (Invitrogen, Carlsbad Calif. cat #13778-150) to 5 µl of siRNA duplexes per well into a 96-well plate and incubated at room temperature for 15 minutes. Subsequently, 80 µl of complete growth media without antibiotic containing ~2×10⁴ Hep3B cells were then added to the siRNA mixture. Cells were incubated for 24 hours prior to RNA purification. Single dose experiments were performed at 10 nM and 0.1 nM final duplex concentration.

Total RNA Isolation Using DYNABEADS mRNA Isolation Kit (Invitrogen, Part #: 610-12)

Cells were harvested and lysed in 150 µl of Lysis/Binding Buffer then mixed for 5 minute at 850 rpm using a platform shaker (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After the supernatant was removed, the lysed cells were added to the remaining beads and mixed for 5 minutes. After the supernatant was removed, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 75° C. Beads were captured on magnet for 5 minutes, and 50 µl of supernatant containing the purified RNA was removed and added to a new 96 well plate.

Real Time PCR

Two µl of cDNA was added to a master mix containing 0.5 µl human GAPDH TaqMan Probe (Applied Biosystems Cat #4326317E), 0.5 µl human TMPRSS6 TaqMan probe (Applied Biosystems cat # Hs00542184_m1) and 5 µl Lightcycler 480 probe master mix (Roche Cat #04887301001) per well in a 384 well plate (Roche cat #04887301001). Real time PCR was performed in a Roche LC480 Real Time PCR system (Roche) using the ΔΔCt(RQ) assay. Each duplex was tested in two independent transfections and each transfection was assayed in duplicate, unless otherwise noted.

To calculate relative fold change, real time data were analyzed using the ΔΔCt method and normalized to assays performed with cells transfected with 10 nM AD-1955, or mock transfected cells.

The sense and antisense sequences of AD-1955 are: SENSE: 5'-cuuAcGcuGAGuAcuucGAdTsdT-3' (SEQ ID NO: 6); and ANTISENSE: 5'-UCGAAGuACUcA-GCGuAAGdTsdT-3' (SEQ ID NO: 7).

TABLE B

Abbreviations of nucleotide monomers used in nucleic acid sequence representation.

| Abbreviation | Nucleotide(s) |
| --- | --- |
| A | Adenosine-3'-phosphate |
| Ab | beta-L-adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |

TABLE B-continued

Abbreviations of nucleotide monomers used in nucleic acid sequence representation.

| Abbreviation | Nucleotide(s) |
|---|---|
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |
| (A3m) | 3'-O-methyladenosine-2'-phosphate |
| (A3mx) | 3'-O-methyl-xylofuranosyladenosine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| (U3mx) | 3'-O-methylxylouridine-2'-phosphate |
| (Chd) | 2'-O-hexadecyl-cytidine-3'-phosphate |
| (pshe) | Hydroxyethylphosphorothioate |
| (Uhd) | 2'-O-hexadecyl-uridine-3'-phosphate |
| (Tgn) | Thymidine-glycol nucleic acid (GNA) S-Isomer |
| (Cgn) | Cytidine-glycol nucleic acid (GNA) |
| (Chd) | 2'-O-hexadecyl-cytidine-3'-phosphate |
| (Ggn) | 2'-O-hexadecyl-cytidine-3'-phosphate |
| (Agn) | Adenosine-glycol nucleic acid (GNA) |
| P | 5'-phosphate |
| (m5Cam) | 2'-O-(N-methylacetamide)-5-methylcytidine-3'-phosphate |
| (m5Cams) | 2'-O-(N-methylacetamide)-5-methylcytidine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| Y44 | 2-hydroxymethyl-tetrahydrofurane-5-phosphate |

Example 1. Design, Specificity and Efficacy Prediction of Oligonucleotides

Transcripts siRNA design was carried out to identify siRNAs targeting human, rhesus (*Macaca mulatta*), mouse, and rat TMPRSS6 transcripts annotated in the NCBI Gene database (http://www.ncbi.nlm.nih.gov/gene/). Design used the following transcripts from the NCBI RefSeq collection: Human—NM_153609.2; Rhesus—XM_001085203.2 and XM_001085319.1; Mouse—NM_027902.2; Rat—NM_001130556.1. Due to high primate/rodent sequence divergence, siRNA duplexes were designed in several separate batches, including but not limited to batches containing duplexes matching human and rhesus transcripts only; human, rhesus, and mouse transcripts only; human, rhesus, mouse, and rat transcripts only; and mouse and rat transcripts only. All siRNA duplexes were designed that shared 100% identity with the listed human transcript and other species transcripts considered in each design batch (above).

The specificity of all possible 19 mers was predicted from each sequence. Candidate 19 mers that lacked repeats longer than 7 nucleotides were then selected. These 1259 candidate human/rhesus, 91 human/rhesus/mouse, 37 human/rhesus/mouse/rat, and 810 mouse/rat siRNAs were used in comprehensive searches against the appropriate transcriptomes (defined as the set of NM_ and XM_ records within the human, rhesus, mouse, or rat NCBI Refseq sets) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5' end of the molecule. Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octomer. Heptamer1 was created by adding a 3' A to the hexamer; heptamer2 was created by adding a 5' A to the hexamer; the octomer was created by adding an A to both 5' and 3' ends of the hexamer. The frequency of octomers and heptamers in the human, rhesus, mouse, or rat 3'UTRome (defined as the subsequence of the transcriptome from NCBI's Refseq database where the end of the coding region, the 'CDS', is clearly defined) was pre-calculated. The octomer frequency was normalized to the heptamer frequency using the median value from the range of octomer frequencies. A 'mirSeedScore' was then calculated by calculating the sum of ((3× normalized octomer count)+(2× heptamer2 count)+(1× heptamer1 count)).

Both siRNA strands were assigned to a category of specificity according to the calculated scores: a score above 3 qualified as highly specific, equal to 3 as specific and between 2.2 and 2.8 qualified as moderately specific. The siRNAs were sorted by the specificity of the antisense strand. Duplexes from the human/rhesus and mouse/rat sets whose antisense oligos lacked GC at the first position, lacked G at both positions 13 and 14, and had 3 or more Us or As in the seed region (characteristics of duplexes with high predicted efficacy) were then selected. Similarly, duplexes from the human/rhesus/mouse and human/rhesus/mouse/rat sets that had had 3 or more Us or As in the seed region were selected.

Candidate GalNAc-conjugated duplexes, 21 and 23 nucleotides long on the sense and antisense strands respectively, were designed by extending antisense 19 mers 4 additional nucleotides in the 3' direction (preserving perfect complementarity with the target transcript). The sense strand was specified as the reverse complement of the first 21 nucleotides of the antisense 23 mer. Duplexes were selected that maintained perfect matches to all selected species transcripts across all 23 nucleotides.

siRNA Sequence Selection

A total of 39 sense and 39 antisense derived human/rhesus, 6 sense and 6 antisense derived human/rhesus/mouse, 3 sense and 3 antisense derived human/rhesus/mouse/rat, and 16 sense and 16 antisense derived mouse/rat siRNA 21/23 mer oligos were synthesized and formed into GalNAc-conjugated duplexes and analyzed for activity.

Example 2. In Vitro Single Dose Screen

The modified and conjugated TMPRSS6 siRNA duplexes were also evaluated for efficacy by transfection assays in human cell line Hep3B. TMPRSS6 siRNAs were transfected at two doses, 10 nM and 0.1 nM. These assays identified duplex AD-59473 (sense UfscsUfgGfuAfuUfUfCfcUfaGf-gGfuAfcAfL96 (SEQ ID NO:8; antisense usGfsuAfcCfcUf-aGfgaaAfuAfcCfaGfasgsu (SEQ ID NO:9)) for further analysis.

Example 3. In Vivo Single Dose Screen Using AD-59743

The ability of AD-59743 to suppress expression of TMPRSS6 protein was assessed by measuring levels of TMPRSS6 and hepcidin mRNA in the liver of wild-type C57BL/6 mice following administration of AD-59743. A single dose of 1, 3 or 10 mg/kg of AD-59743 was administered subcutaneously, and the mice were sacrificed on day 3 or day 7. Levels of TMPRSS6 and hepcidin mRNA in the liver were measured by qPCR using the methods described above. A control group received injections with PBS.

Figure 2:
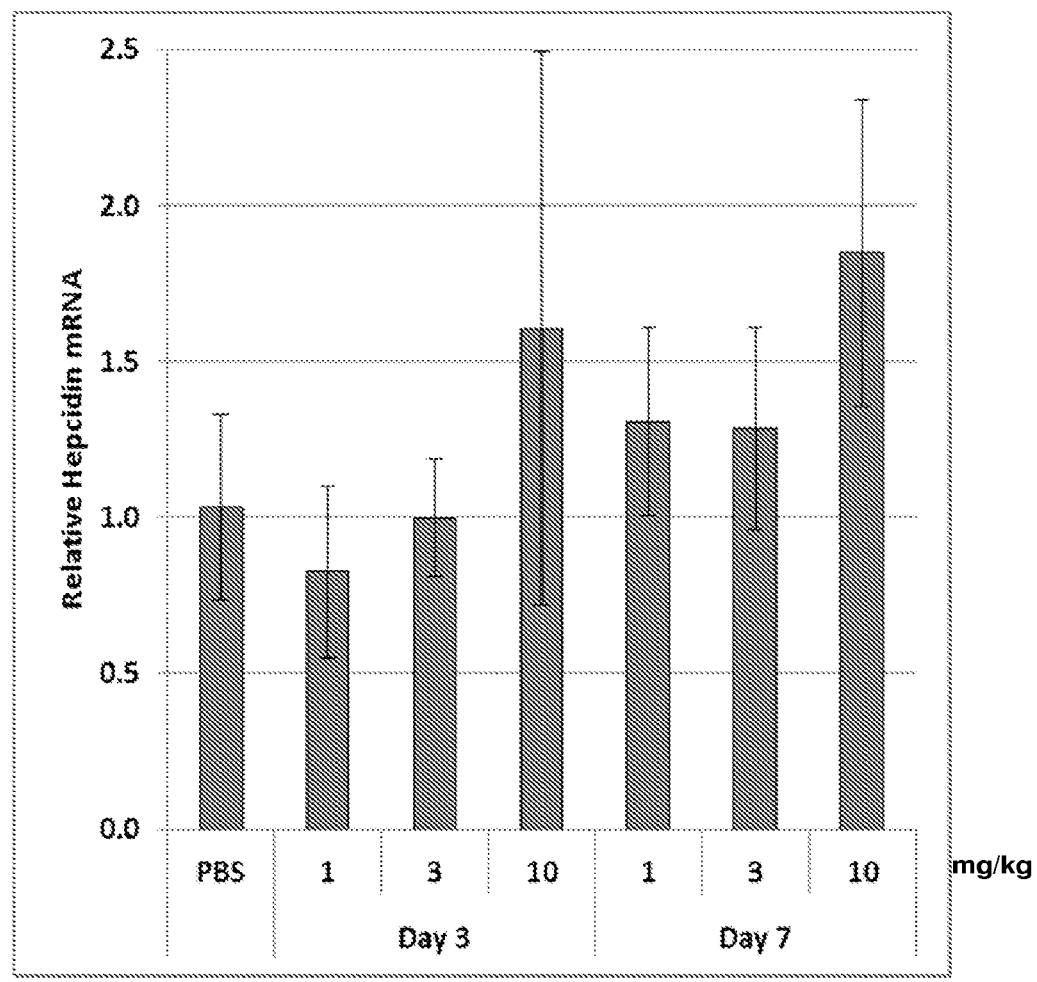
FIG. 2 is a graph showing relative levels of hepcidin mRNA in the liver of wild-type mice following administration of a single dose of 1 mg/kg, 3 mg/kg, or 10 mg/kg of the iRNA agent AD-59743.

The levels of TMPRSS6 mRNA following administration of AD-59743 are shown in FIG. 1, and the levels of hepcidin mRNA following administration of AD-59743 are shown in FIG. 2. The results demonstrate a dose-dependent decrease in the levels of TMPRSS6 transcripts that is sustained through day 7.

Example 4. In Vivo Effect of TMPRSS6 iRNA Agents in Combination with an Iron Chelator The purpose of this study was to test the effect of co-administered TMPRSS6 specific siRNA and iron chelators on iron levels. In the study, 6-week old wild-type C57BL/6 and thalassemic Th3/+ mice (Douet et al., *Am. J. Pathol.* (2011), 178(2):774-83) were fed low-iron diets containing 3-5 ppm iron. The mice were administered intravevously the formulation AF-011-46273 containing deferiprone, an iron chelator at a dose of 250 mg/kg/day and the iRNA agent AD-46273 with the following structure: oligoSeq-sense—uGGuAuuuccuAGGGuAcAdTsdT (SEQ ID NO:10); oligoSeq-antisense—UGuACCCuAGGAAAuAC-cAdTsdT (SEQ ID NO:11). The formulation also contained MC-3/DSPC/Cholesterol/PEG-DMG 50/10/38.5/1.5. Liver and spleen tissues were collected and tissue nonheme iron concentrations were determined as described previously (see, e.g., Schmidt et al. (2013) *Blood* 121(7):1200-8; Cook, J D, et al. *Tissue iron stores*. In: Cook J D, editor. *Methods in Hematology*. Vol 1. New York, N.Y.: Churchill Livingstone Press; 1980. p. 104-109).

The results of these experiments demonstrate an additive effect of AD-46273 and deferiprone in Th3/+ mice, with the decreased iron levels relative to the negative controls.

Example 5. Design, Specificity and Efficacy Prediction of Oligonucleotides

Transcripts siRNA design was carried out to identify siRNAs targeting human, cynomolgus monkey (*Macaca fascicularis*; henceforth "cyno"), mouse, and rat TMPRSS6 transcripts annotated in the NCBI Gene database (http://www.ncbi.nlm.nih.gov/gene/). Design used the following transcripts from the NCBI RefSeq collection: Human—NM_153609.2; Mouse—NM_027902.2; Rat—NM_001130556.1. For cyno, a transcript sequence was obtained via alignment with human TMPRSS6 of sequence assembled from two accessions: "ENSP00000384964 [mRNA] locus=chr10:82446450:82485403:-" and FR874253.1, available from the *M. fascicularis* genome project and NCBI Nucleotide databases, respectively (http://macaque.genomics.org.cn/page/species/download.jsp and http://www.ncbi.nlm.nih.gov/nucleotide/) using the method provided above.

siRNA Sequence Selection

A total of 5 sense and 5 antisense human, 32 sense and 32 antisense derived human/cyno, 4 sense and 4 antisense derived human/cyno/mouse, 8 sense and 8 antisense derived human/cyno/mouse/rat, 19 sense and 19 antisense derived human/cyno/rat, 2 sense and 2 antisense derived human/mouse, and 1 sense and 1 antisense derived human/mouse/rat siRNA 21/23 mer oligos were synthesized and formed into GalNAc-conjugated duplexes and analyzed for activity.

The sequences of a subset of the sense and antisense strands of the unmodified duplexes designed are shown in Table 1, and the sequences of those sense and antisense strands of the modified duplexes are shown in Table 2. Sequences for AD-46273.1 and AD-59743.1 identified in earlier screens are provided in the tables for reference.

TABLE 1

TMPRSS6-unmodified sequences

| Duplex ID | Sense sequence ID | Sense sequence (5' to 3') | SEQ ID NO: | Antisense sequence ID | Antisense sequence (5' to 3') | SEQ ID NO: | Position in NM_153609.2 |
|---|---|---|---|---|---|---|---|
| AD-46273.1 | A-96908.1 | UGGUAUUUCCUAGGGUACATT | 12 | A-96909.1 | UGUACCCUAGGAAAUACCATT | 20 | 324 |
| AD-59743.1 | A-120243.1 | UCUGGUAUUUCCUAGGGUACA | 13 | A-120244.1 | UGUACCCUAGGAAAUACCAGAGU | 21 | 326 |
| AD-60940.1 | A-122745.1 | CUGGUAUUUCCUAGGGUACAA | 14 | A-122746.1 | UUGUACCCUAGGAAAUACCAGAG | 22 | 327 |
| AD-60944.1 | A-122732.1 | GGUGCUACUCUGGUAUUUCCU | 15 | A-122733.1 | AGGAAAUACCAGAGUAGCACCCC | 23 | 318 |
| AD-60998.1 | A-122821.1 | CACUGUGACUGUGGCCUCCAA | 16 | A-122822.1 | UUGGAGGCCACAGUCACAGUGCU | 24 | 1804 |
| AD-61001.1 | A-122823.1 | CACCUCCCAGAUCUCCCUCAA | 17 | A-122824.1 | UUGAGGGAGAUCUGGGAGGUGAA | 25 | 1413 |
| AD-61002.2 | A-122838.1 | UGGUAUUUCCUAGGGUACAAA | 18 | A-122839.1 | UUUGUACCCUAGGAAAUACCAGA | 26 | 328 |
| AD-61006.1 | A-122856.1 | CCUGCCCUGGAGAGUUCCUCU | 19 | A-122857.1 | AGAGGAACUCUCCAGGGCAGGGG | 27 | 1481 |

TABLE 2

TMPRSS6 modified sequences

| Duplex ID | Sense sequence ID | Sense sequence (5' to 3') | SEQ ID NO: | Antisense sequence ID | Antisense sequence (5' to 3') | SEQ ID NO: |
|---|---|---|---|---|---|---|
| AD-46273.1 | A-96908.1 | uGGuAuuccuAGGGuAcAdTsdT | 28 | A-96909.1 | UGuACCCuAGGAAuACcAdTsdT | 36 |
| AD-59743.1 | A-120243.1 | UfscsUfgGfuAfuUfuCfcCfuaGfgGfuAfcAfL96 | 29 | A-120244.1 | usGfsuAfcCfcUfaGfgaaAfuAfcCfaGfasgsu | 37 |
| AD-60940.1 | A-122745.1 | CfsusGfgUfaUfuUfcCfcUfaAfgGfgUfaCfaAfL96 | 30 | A-122746.1 | usUfsgUfaCfcCfcUfaFggaAfuAfuAfcCfAfgsasg | 38 |
| AD-60944.1 | A-122732.1 | GfsgsUfgCfuAfcUfcUfggGfuAfuUfuCfcUfL96 | 31 | A-122733.1 | asGfsgAfaAfuAfcCfagaGfuAfgCfaCfcscsc | 39 |
| AD-60998.1 | A-122821.1 | CfsasCfuGfuGfacUfgGfuGfcCfcCfaAfL96 | 32 | A-122822.1 | usUfsgGfaGfgCfcAfcagUfcAfcAfgUfgscsu | 40 |
| AD-61001.1 | A-122823.1 | CfsasCfcUfcCfcAfGfaUfcCfuUfcCfuCfaAfL96 | 33 | A-122824.1 | usUfsgAfgGfgAfgAfucuGfgGfaGfgUfgsasa | 41 |
| AD-61002.1 | A-122838.1 | UfsgsGfuAfuUfuCfcUfUfaGfgGfuAfcAfaAfL96 | 34 | A-122839.1 | usUfsuGfuAfcCfcUfaggAfaAfuAfcCfasgsa | 42 |
| AD-61006.1 | A-122856.1 | CfscsUfgCfcCfuGfEfaAfgAfgUfUfcCfcUfL96 | 35 | A-122857.1 | asGfsaGfaAfaCfuCfuccAfgGfgCfaGfgsgsg | 43 |

Example 6. In Vitro Single Dose Screen

In vitro screening of the duplexes was performed in Hep3B cells as described above. The results are shown in Table 3.

TABLE 3

TMPRSS6 single dose screen.

| Duplex ID | Avg 10 nm | Avg 0.1 nM | SD 10 nM | SD 0.1 nM |
|---|---|---|---|---|
| AD-46273 | 76.5 | 112.1 | 14.3 | 18.6 |
| AD-59743 | 61.4 | 108.2 | 8.7 | 4.4 |
| AD-60940 | 24.2 | 22.6 | 10.1 | 9.7 |
| AD-60944 | 24.6 | 78.5 | 1.1 | 36.5 |
| AD-60998 | 32.6 | 61.4 | 5.7 | 24.6 |
| AD-61001 | 57.9 | 85.2 | 8.1 | 42.0 |
| AD-61006 | 31.7 | 70.9 | 7.8 | 6.6 |

Example 7. In Vivo Effect of Single Dose Administration of TMPRSS6 iRNA Agent Female C57BL/6 mice were administered a single subcutaneous injection of AD-60940 at a dose of 0.3 mg/kg, 1.0 mg/kg, or 3.0 mg/kg, or PBS alone as a control. Three mice were evaluated per dose for hepatic TMPRSS6 mRNA, hepatic hepcidin mRNA, serum hepcidin, total serum iron, and percent transferrin saturation at various time points. Mice receiving 1.0 mg/kg or 3.0 mg/kg of AD-60940 or PBS were evaluated at day 0 (pre-treatment) and 7, 11, 14 and 21 days after treatment. Mice receiving 0.3 mg/kg AD-60940 were evaluated at day 0 (pre-treatment) and at 7 and 11 days after treatment. Hepatic TMPRSS6 mRNA and hepatic hepcidin mRNA levels were determined by qPCR, normalized to GAPDH mRNA levels, and expressed relative to the mRNA levels in mice administered PBS alone. Serum hepcidin was measured by ELISA (Intrinsic Life Sciences). Total serum iron and percent transferrin saturation (% TfSat) were measured using an Olympus AU400 Serum Chemistry Analyzer. Each data point represents the mean value from three mice. The standard deviation of the mean is represented by error bars.

Figure 3A:
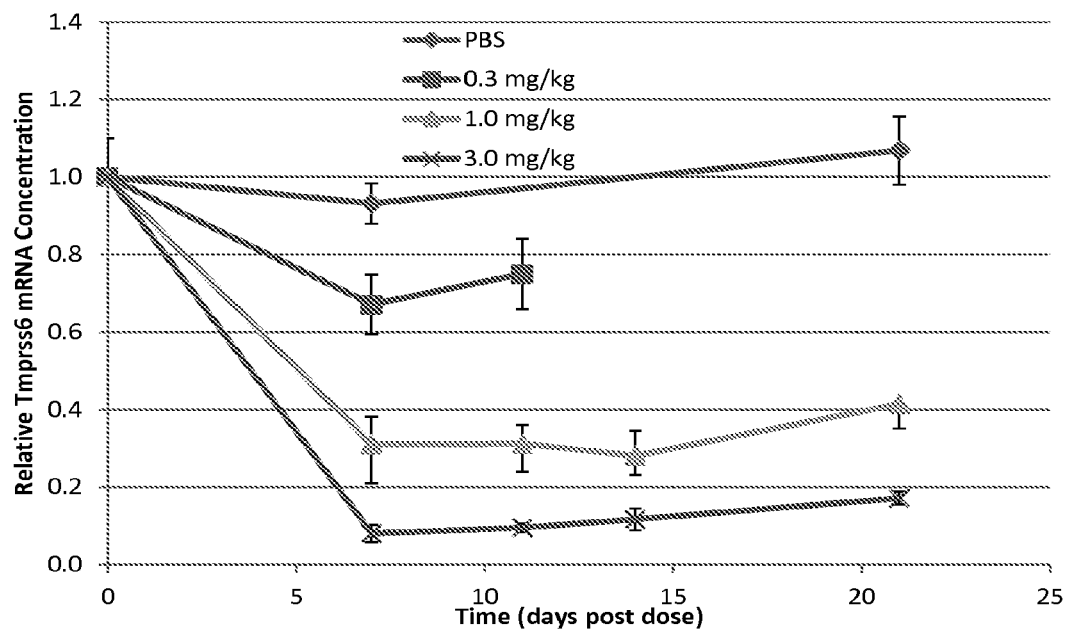
FIG. 3A is a graph depicting the level of hepatic TMPRSS6 mRNA in C57BL/6 mice at various time points following a single subcutaneous injection of AD-60940 at a dose of 0.3 mg/kg, 1.0 mg/kg, or 3.0 mg/kg, or PBS alone (control). Each data point represents the mean value from three mice. The standard deviation of the mean is represented by error bars.
Figure 3B:
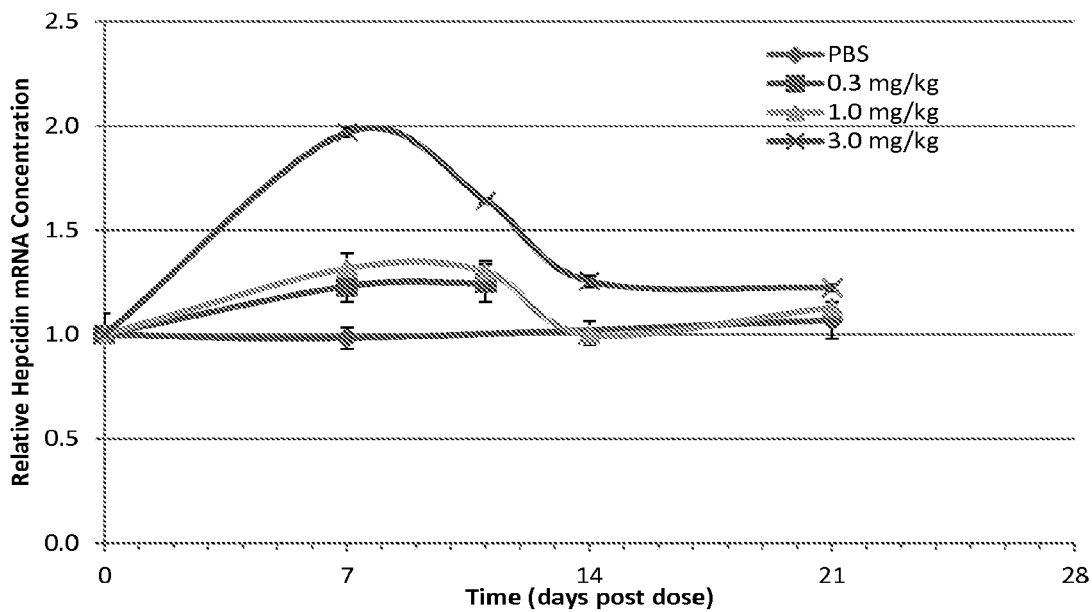
FIG. 3B is a graph depicting the level of hepatic hepcidin mRNA in C57BL/6 mice at various time points following a single subcutaneous injection of AD-60940 at a dose of 0.3 mg/kg, 1.0 mg/kg, or 3.0 mg/kg, or PBS alone (control). Each data point represents the mean value from three mice. The standard deviation of the mean is represented by error bars.
Figure 3C:
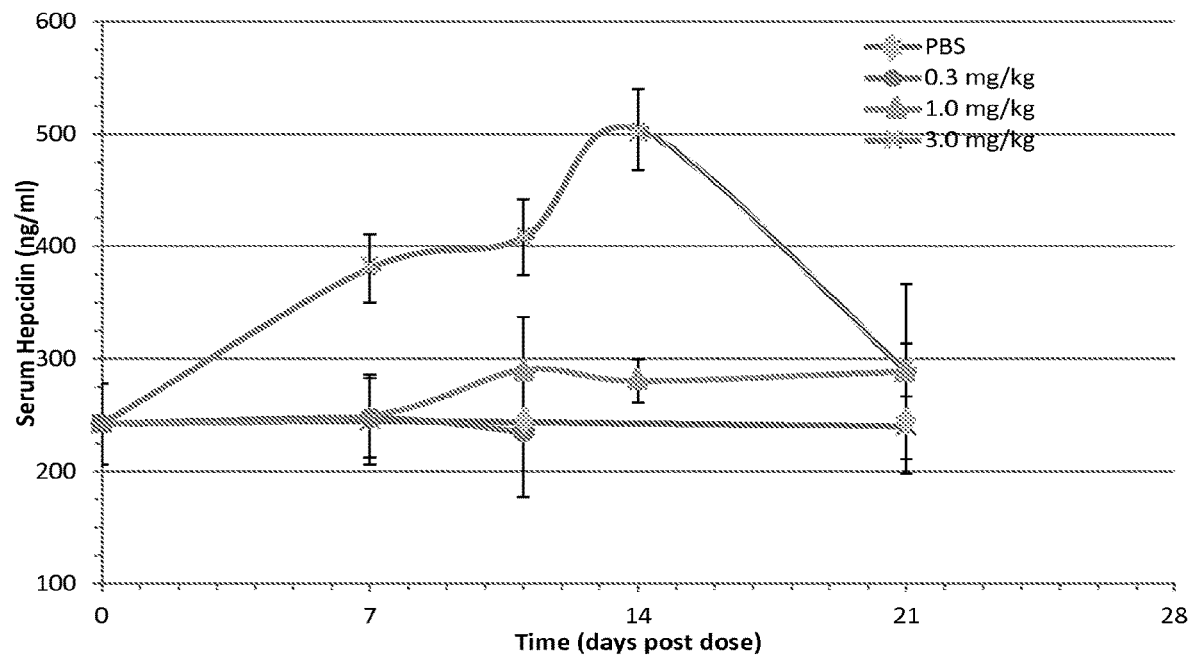
FIG. 3C is a graph depicting the level of serum hepcidin in C57BL/6 mice at various time points following a single subcutaneous injection of AD-60940 at a dose of 0.3 mg/kg, 1.0 mg/kg, or 3.0 mg/kg, or PBS alone (control). Each data point represents the mean value from three mice. The standard deviation of the mean is represented by error bars.
Figure 3D:
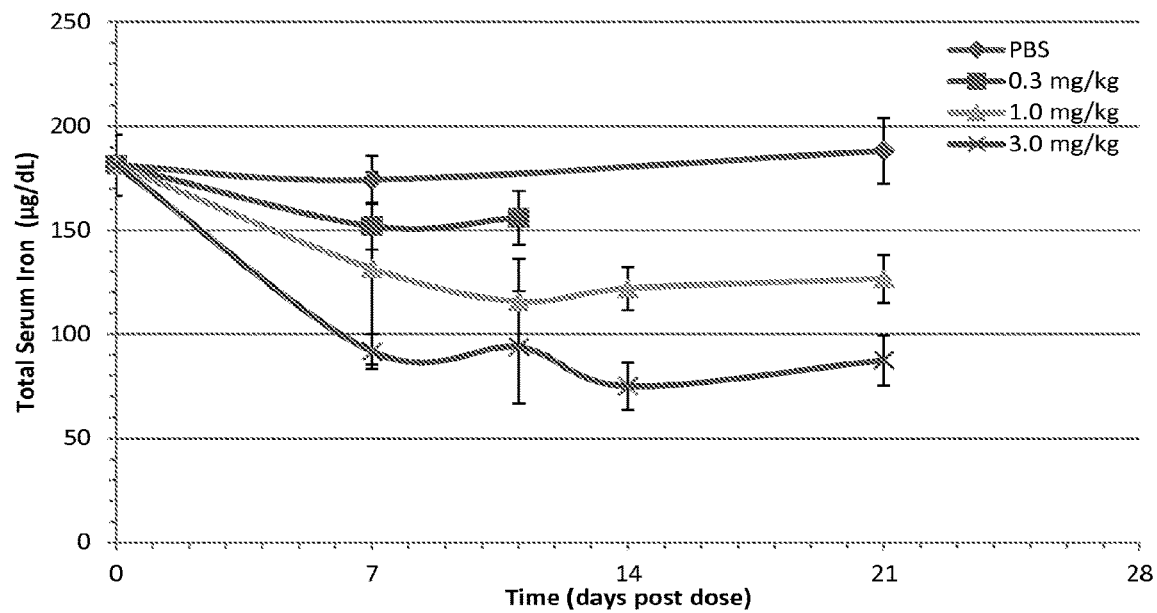
FIG. 3D is a graph depicting the level of total serum iron in C57BL/6 mice at various time points following a single subcutaneous injection of AD-60940 at a dose of 0.3 mg/kg, 1.0 mg/kg, or 3.0 mg/kg, or PBS alone (control). Each data point represents the mean value from three mice. The standard deviation of the mean is represented by error bars.
Figure 3E:
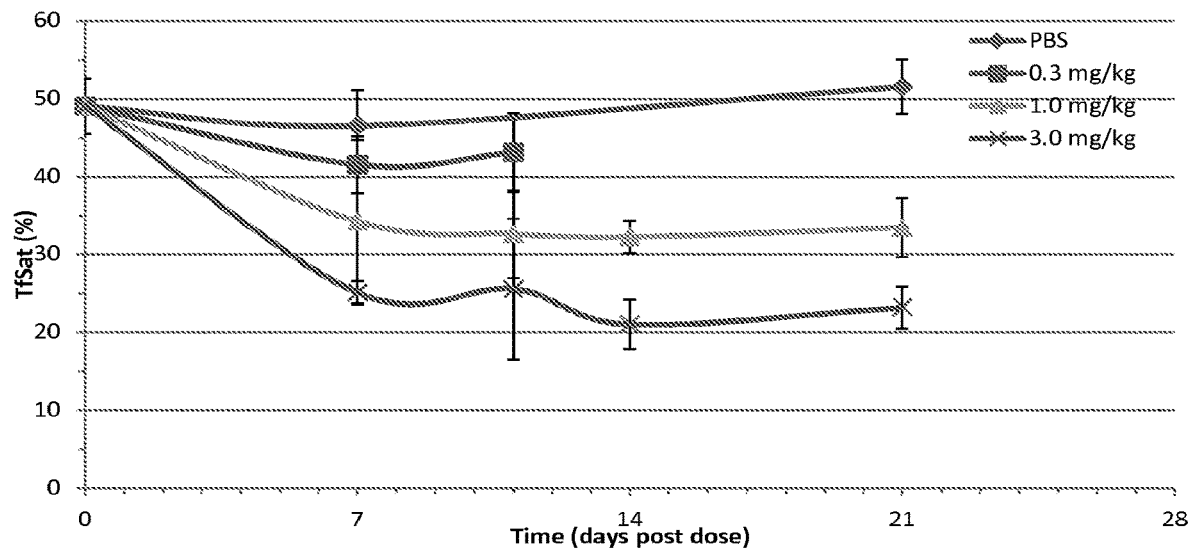
FIG. 3E is a graph depicting the level of percent transferrin saturation in C57BL/6 mice at various time points following a single subcutaneous injection of AD-60940 at a dose of 0.3 mg/kg, 1.0 mg/kg, or 3.0 mg/kg, or PBS alone (control). Each data point represents the mean value from three mice. The standard deviation of the mean is represented by error bars.
Figure 3F:
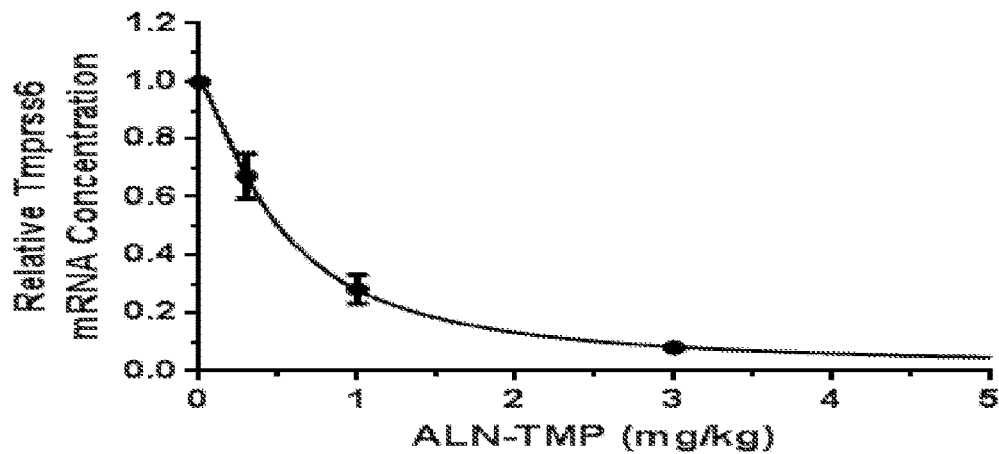
FIG. 3F is a graph depicting the relative hepatic TMPRSS6 mRNA concentration as a function of AD-60940 dose at 11 days following administration. Each data point represents the maximum suppression of TMPRSS6 mRNA concentration observed at each dose level. The data were fit to the Hill equation.

Single dose administration of AD-60940 resulted in robust and durable suppression of hepatic TMPRSS6 mRNA relative to the control. TMPRSS6 mRNA concentration was suppressed by greater than 90% for up to three weeks following administration of the 3.0 mg/kg dose (FIG. 3A). As a result of the suppression of hepatic TMPRSS6 mRNA concentration, hepcidin mRNA levels, increased two-fold relative to the control (FIG. 3B), and serum hepcidin concentration increased greater than 2-fold relative to the control (FIG. 3C). In addition, total serum iron (FIG. 3D) decreased and percent transferrin saturation decreased by greater than 50% relative to the control (FIG. 3E). The decreases in total serum iron and percent transferrin saturation were durable for up to three weeks following administration of AD-60940. FIG. 3F demonstrates the relative hepatic TMPRSS6 mRNA concentration as a function of AD-60940 dose at 11 days following administration. Each data point represents the maximum suppression of TMPRSS6 mRNA concentration observed at each dose level. The data were fit to the Hill equation.

The degree to which AD-60940 modulates hepcidin and serum iron mobilization is nearly identical to that observed in the previous Hbb$^{th3/+}$ mouse studies (Schmidt et al., *Blood* (2013), 121(7), 1200-1208) and indicates that AD-60940 is a potent RNAi therapeutic for producing disease modifying effects in β-thalassemia.

Figure 4A:
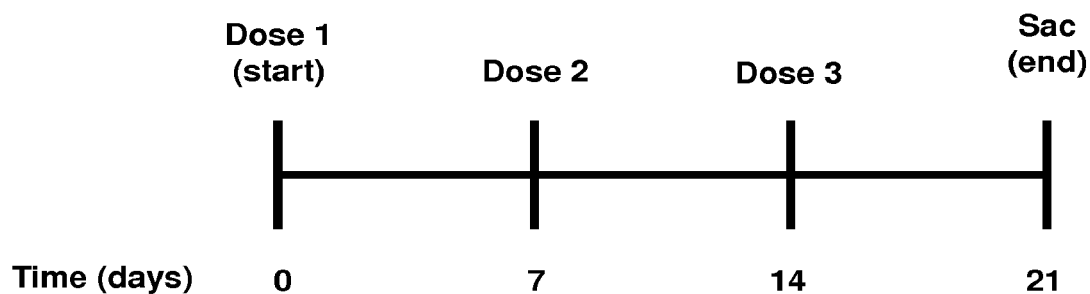
FIG. 4A is a schematic depicting the administration regimen of one dose per week for three weeks followed by sacrifice of the mice at day 21.

Example 8. In Vivo Effect of Multi-Dose Administration of TMPRSS6 iRNA Agent Female C57BL/6 mice were administered a subcutaneous injection of AD-60940 at a dose of 0.3 mg/kg, 1.0 mg/kg, or PBS alone (as a control) once per week for three weeks then sacrificed 7 days after the final dose (FIG. 4A). Three mice per dose were evaluated for hepatic TMPRSS6 mRNA, hepatic hepcidin mRNA, and percent transferrin saturation. Hepatic TMPRSS6 mRNA and hepatic hepcidin mRNA levels were determined by qPCR, normalized to GAPDH mRNA levels and expressed relative to the mRNA levels in mice administered PBS alone. Percent transferrin saturation (% TfSat) was measured using an Olympus AU400 Serum Chemistry Analyzer. Each data point represents the mean value from three mice. The standard deviation of the mean is represented by error bars.

Figure 4B:
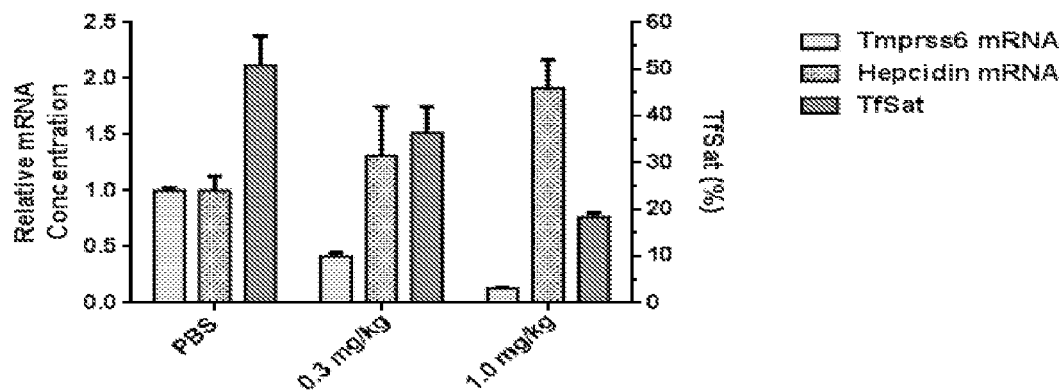
FIG. 4B is a graph showing the levels of hepatic TMPRSS6 mRNA, hepatic hepcidin mRNA, and percent transferrin saturation in C57BL/6 mice administered a subcutaneous injection of AD-60940 at a dose of 0.3 mg/kg or 1.0 mg/kg, or PBS (control) according to the regimen shown in FIG. 4A. Each bar represents the mean value from three mice. The standard deviation of the mean is represented by error bars.
Figure 4C:
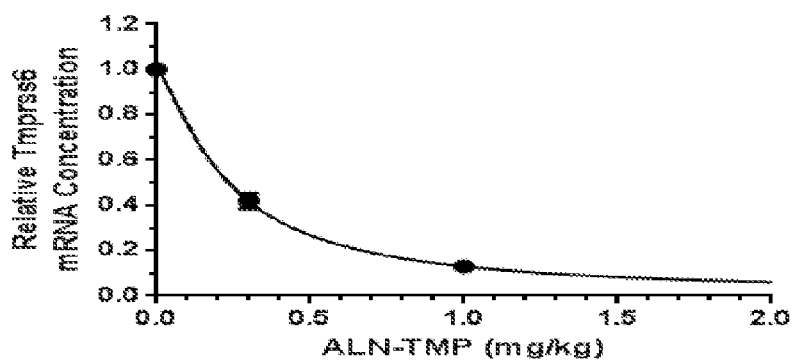
FIG. 4C demonstrates the relative hepatic TMPRSS6 mRNA concentration as a function of AD-60940 dose. The data were fit to the Hill equation.

Multi-dose administration of 1.0 mg/kg AD-60940 resulted in greater than 90% suppression of TMPRSS6 mRNA concentration (FIG. 4B). Hepcidin mRNA concentration increased two-fold and percent transferrin saturation decreased by greater than 50% relative to the control (FIG. 4B). FIG. 4C demonstrates the relative hepatic TMPRSS6 mRNA concentration as a function of AD-60940 dose. The data were fit to the Hill equation. These data indicate that the multi-dose ED80 is less than 1.0 mg/kg.

This study demonstrates that AD-60940 exhibits robust and durable suppression of TMPRSS6, resulting in hepcidin induction and systemic iron restriction and indicates that AD-60940 is a potent RNAi therapeutic for producing disease modifying effects in β-Thalassemia.

Figure 5A:
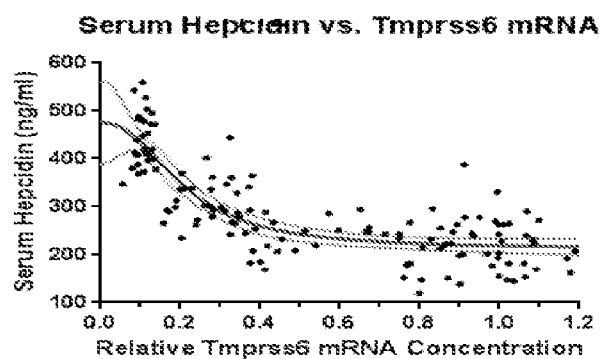
FIG. 5A is a graph depicting the relationship between serum hepcidin concentration and relative TMPRSS6 mRNA levels.
Figure 5B:
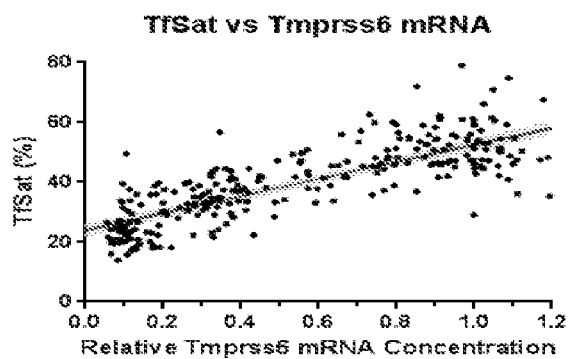
FIG. 5B is a graph depicting the relationship between percent transferrin saturation and relative TMPRSS6 mRNA level.
Figure 5C:
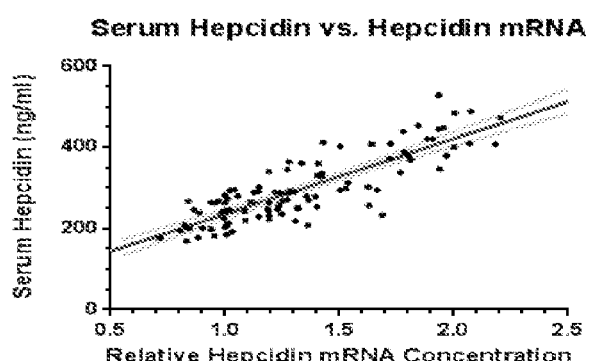
FIG. 5C is a graph depicting the relationship between serum hepcidin concentration and relative hepcidin mRNA levels.
Figure 5D:
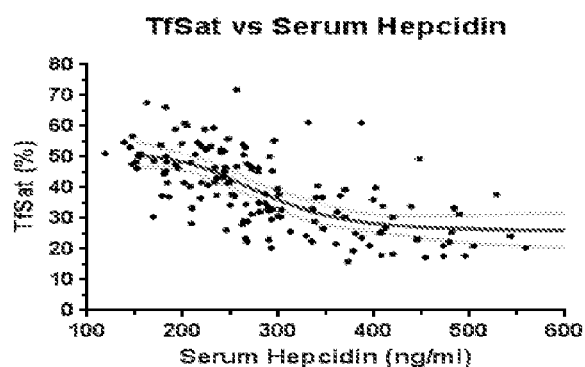
FIG. 5D is a graph depicting the relationship between percent transferrin saturation and serum hepcidin concentration.

Example 9. Relationship Between Liver TMPRSS6 mRNA Levels and Serum Hepcidin Concentration and Percent Transferrin Saturation Data generated using AD-59743, AD-61002, AD-60940, and other TMPRSS6 iRNA agents were further analyzed to evaluate the relationship between liver TMPRSS6 mRNA levels and serum hepcidin levels and percent transferrin saturation. Serum hepcidin concentration demonstrated a non-linear relationship to TMPRSS6 mRNA levels using the Hill equation (FIG. 5A). The percent transferrin saturation demonstrated a linear relationship to TMPRSS6 mRNA levels when fit to a simple linear regression equation (FIG. 5B). The linear relationship between TMPRSS6 mRNA levels and percent transferrin saturation indicate that iron restriction can be precisely and predictably modulated by AD-60940. Serum hepcidin concentration and relative hepcidin mRNA levels also demonstrated a linear relationship when fit to a simple linear regression equation (FIG. 5C). In contrast, the relationship between percent transferrin saturation and serum hepcidin concentration was non-linear and fit to the Hill equation (FIG. 5D).

Example 10. In Vivo Single Dose Screen

Figure 6:
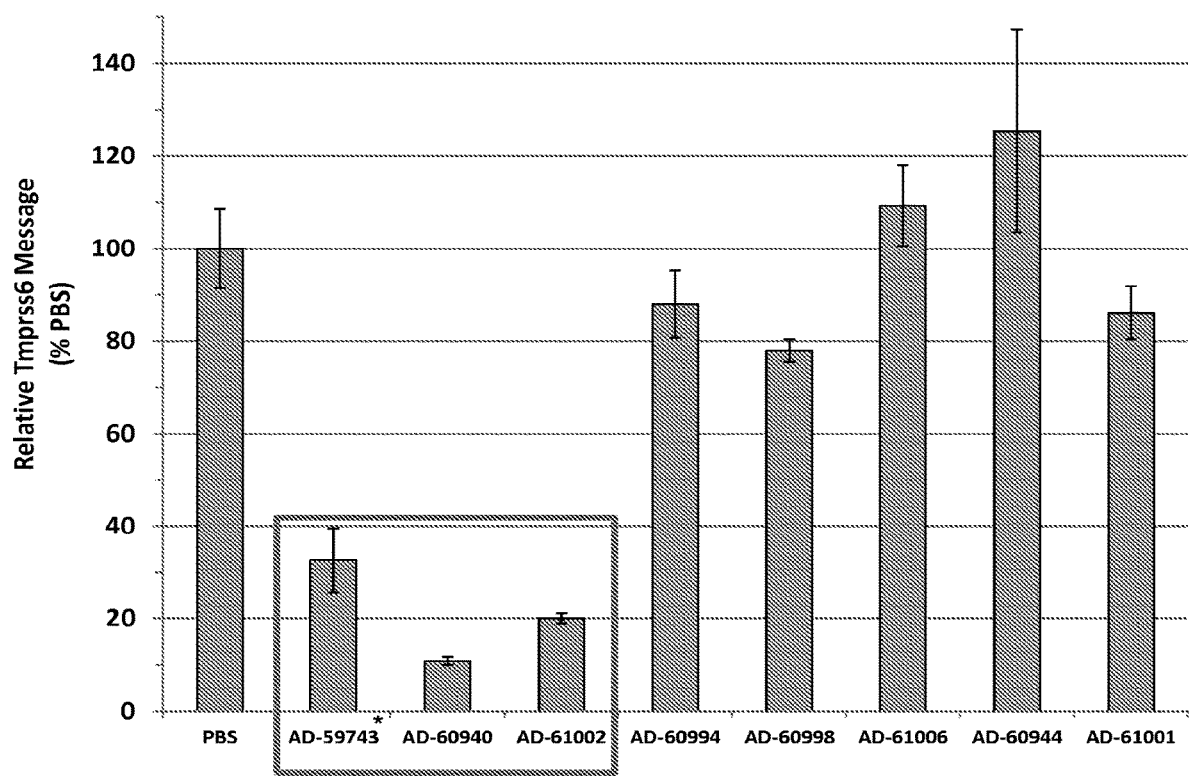
FIG. 6 is a graph showing relative levels of TMPRSS6 mRNA in the liver of C57BL/6 mice following administration of a single subcutaneous dose of 3 mg/kg of the indicated iRNA agent or PBS (control). The bars represent the mean from three mice and the error bars represent the standard deviation of the mean.

TMPRSS6 siRNA duplexes as indicated in FIG. 6 were evaluated for efficacy by their ability to suppress levels of TMPRSS6 mRNA in the liver of female C57BL/6 mice following administration of the siRNA duplex. A single subcutaneous dose of 3 mg/kg of TMPRSS6 siRNA duplex was administered, and the mice were sacrificed 7 days later.

The level of TMPRSS6 mRNA in the liver was measured by qPCR using the methods described above. Mice in a control group received an injection of PBS.

The levels of TMPRSS6 mRNA following administration of a TMPRSS6 siRNA duplex are shown in FIG. 6. The results demonstrate that administration of AD-60940, AD-59743 and AD-61002 resulted in substantial suppression of liver TMPRSS6 mRNA with AD60940 producing the greatest silencing. Specifically, TMPRSS6 siRNA duplex AD-60940 reduced TMPRSS6 mRNA by greater than 80% relative to the control. The data also demonstrate that treatment with AD-59743, AD-60940, AD-61002, AD-60994, AD-60998, and AD-61001 result in a decrease in the level of TMPRSS6 transcript that is maintained through day 7.

Example 11. In Vivo Multi-Dose Screen

Figure 7:
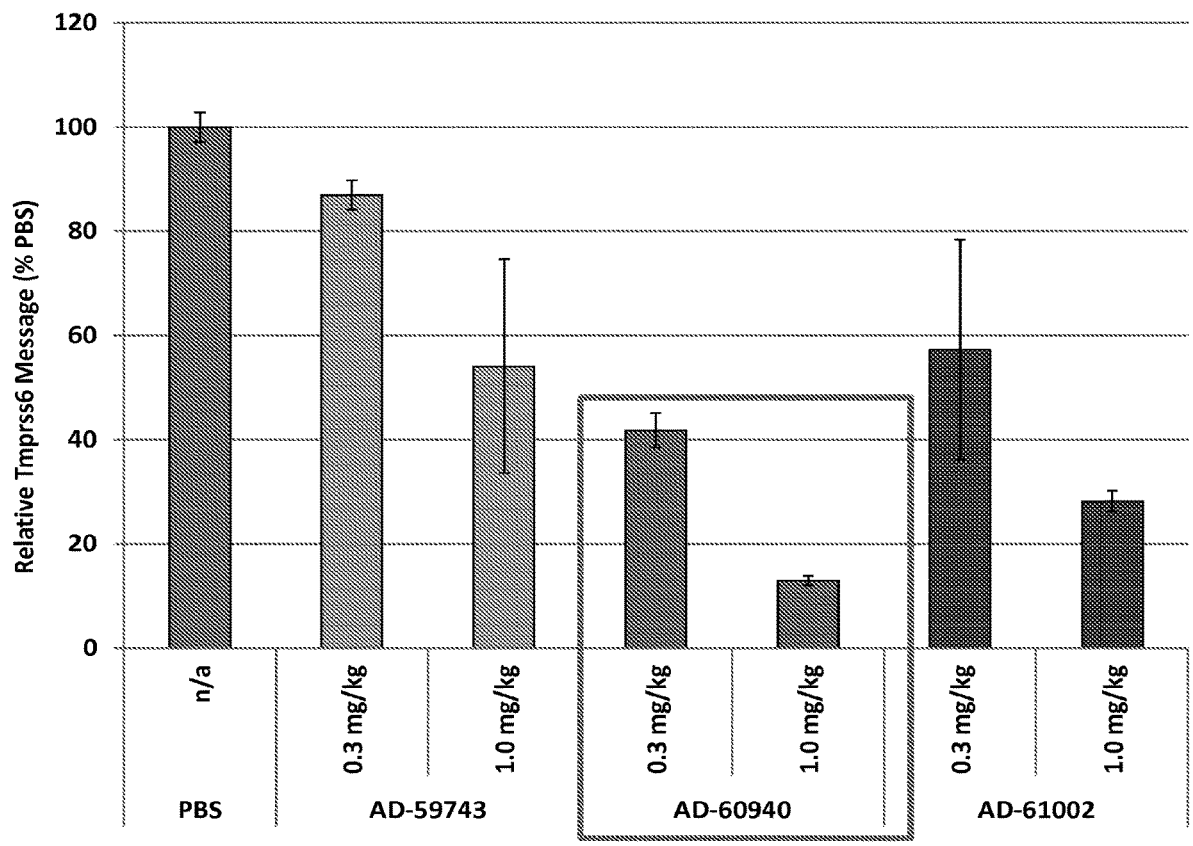
FIG. 7 is a graph showing relative levels of TMPRSS6 mRNA in the liver of C57BL/6 mice following a subcutaneous dose of 0.3 mg/kg or 1.0 mg/kg of the indicated iRNA agent, or PBS (control), once a week for three weeks. The bars represent the mean from three mice and the error bars represent the standard deviation of the mean.
Figure 9A:
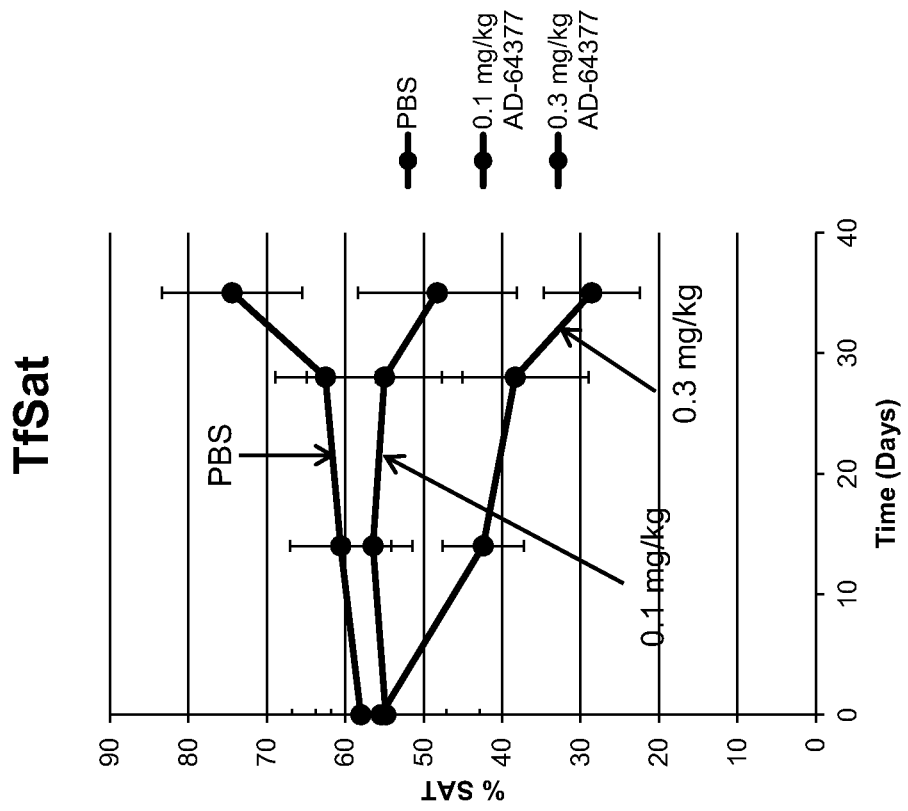
FIG. 9A is a bar graph depicting the relative levels of TMPRSS6 mRNA in the liver of C57BL/6 mice following administration of a 1 time weekly for five weeks subcutaneous dose of 0.1 mg/kg or 0.3 mg/kg of the indicated iRNA agents or PBS (control). The points represent the mean from three mice at each time point and the error bars represent the standard deviation of the mean.
Figure 9B:
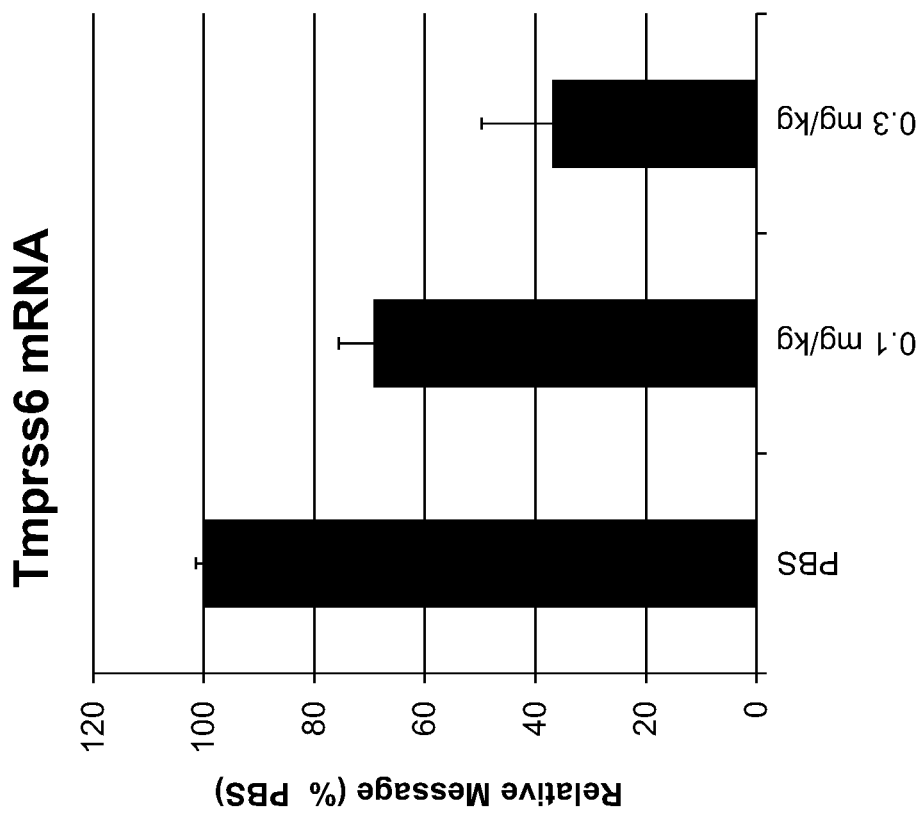
FIG. 9B is a graph depicting the relative levels of transferrin saturation in C57BL/6 mice on the indicated days following administration of a 1 time weekly for five weeks subcutaneous dose of 0.1 mg/kg or 0.3 mg/kg subcutaneous dose of the indicated iRNA agents or PBS (control). The points represent the mean from three mice at each time point and the error bars represent the standard deviation of the mean.
Figure 9D:
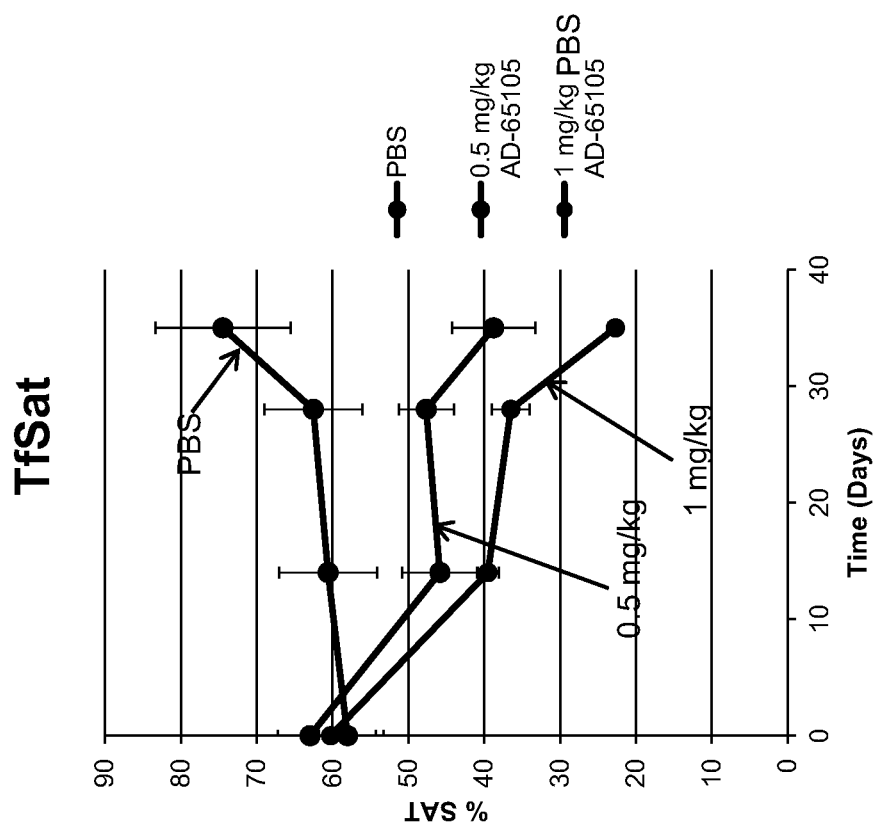
FIG. 9D is a graph depicting the relative levels of transferrin saturation in C57BL/6 mice on the indicated days following administration of a 1 time weekly for five weeks subcutaneous dose of 0.5 mg/kg or 1.0 mg/kg subcutaneous dose of the indicated iRNA agents or PBS (control). The points represent the mean from three mice at each time point and the error bars represent the standard deviation of the mean.
Figure 9C:
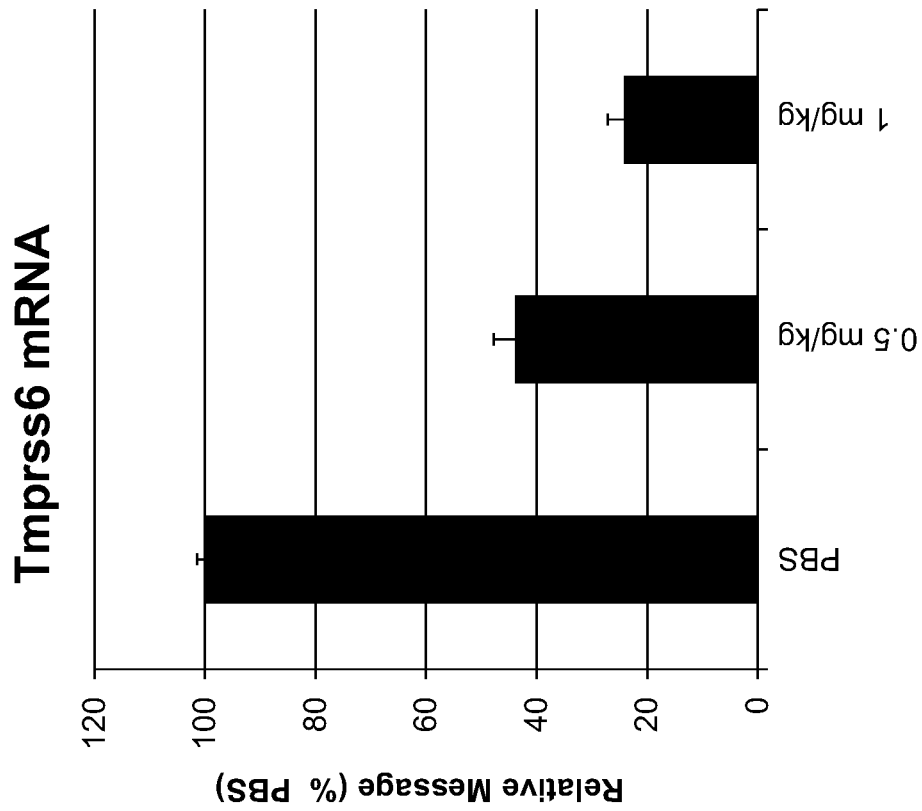
FIG. 9C is a bar graph depicting the relative levels of TMPRSS6 mRNA in the liver of C57BL/6 mice following administration of a 1 time weekly for five weeks subcutaneous dose of 0.5 mg/kg or 1.0 mg/kg of the indicated iRNA agents or PBS (control). The points represent the mean from three mice at each time point and the error bars represent the standard deviation of the mean.

TMPRSS6 siRNA duplexes as indicated in FIG. 7 were evaluated for efficacy by their ability to suppress levels of TMPRSS6 mRNA in the liver of wild-type C57BL/6 mice following administration of the siRNA duplex. A subcutaneous dose of either 0.3 mg/kg or 1.0 mg/kg of TMPRSS6 siRNA duplex was administered once a week for three weeks. The mice were sacrificed 7 days after the last dose. The level of TMPRSS6 mRNA in the liver was measured by qPCR using the methods described above. Mice in a control group received an injection of PBS.

The levels of TMPRSS6 mRNA following administration of a TMPRSS6 siRNA duplex are shown in FIG. 7. The results demonstrate that the 1.0 mg/kg dosing regimen of TMPRSS6 siRNA duplex AD-60940 reduces TMPRSS6 mRNA by greater than 80% relative to the control.

Example 12. Modification of AD-60940

Based on the observation that administration of AD-60940 reduced TMPRSS6 mRNA by greater than 80% relative to the control, additional siRNAs based on the parent sequence of AD-60940 with a variety of chemical modifications were evaluated for efficacy in single dose screens at 10 nM and 0.1 nM by transfection in Hep3B cells as described above. The sequences of the sense and antisense strands of these agents are shown in Table 4 and the results of this screen are shown in Table 5. The data in Table 5 are expressed as the average fraction message remaining relative to control.

Additional chemical modifications were made to the AD-60940 sequence and the duplexes were evaluated for efficacy by their ability to suppress levels of TMPRSS6 mRNA in the liver of female C57BL/6 mice following administration of the siRNA duplex. A single subcutaneous dose of 0.5 mg/kg of TMPRSS6 siRNA duplex was administered, and the mice were sacrificed 14 days later. A subset of the duplexes (AD-60940, AD-64376, AD-64377, AD-64380, and AD-64381) were further evaluated for durability of response at days 14 and 28 after a single subcutaneous dose of 3.0 mg/kg. The level of TMPRSS6 mRNA in the liver was measured by qPCR using the methods described above. Mice in a control group received an injection of PBS.

The results of the first study are shown in Table 6. Substantial mRNA knockdown was observed for a number of the duplexes at the 0.5 mg/kg dose at day 14. Further, in the subset of duplexes tested at the 3.0 mg/kg dose, the knockdown observed at day 14 was sustained through the 28 day time point for all of the duplexes tested.

TABLE 4

TMPRSS6 Modified Sequences based on AD-60940 (SEQ ID NOs: 11 and 12)

| Duplex ID | SenseID | Sense Sequence | SEQ ID NO: | AntisenseID | Antisense Sequence | SEQ ID NO: |
|---|---|---|---|---|---|---|
| AD-63240 | A-122745.11 | CfsusGfgUfaUfuUfCfCfCfuAfgGfgUfacCfaAfL96 | 44 | A-126607.1 | usUfsguaCfcCfuAfggaAfaUfaCfcAfgsasg | 53 |
| AD-63209 | A-126594.1 | csusgguaUfuUfCfCfuaggGfdTacaaL96 | 45 | A-122746.13 | usUfsgUfaCfcCfuAfggaAfaUfaCfcAfgsasg | 54 |
| AD-63223 | A-122745.16 | CfsusGfgUfaUfuUfCfCfCfuAfgGfgUfacCfaAfL96 | 46 | A-126612.1 | usUfsguaCfccuaggaAfaUfaccasgsasg | 55 |
| AD-63226 | A-126589.1 | csusgguaUfuUfCfCfuaggGfuacaaL96 | 47 | A-122746.8 | usUfsgUfaCfcCfuAfggaAfaUfaCfcAfgsasg | 56 |
| AD-60940 | A-122745.1 | CfsusGfgUfaUfuUfCfCfCfuAfgGfgUfacCfaAfL96 | 48 | A-122746.1 | usUfsgUfaCfcCfuAfggaAfaUfaCfcAfgsasg | 57 |
| AD-63240 | A-122745.11 | CfsusGfgUfaUfuUfCfCfCfuAfgGfgUfacCfaAfL96 | 49 | A-122746.13 | usUfsgUfaCfcCfuAfggaAfaUfaUfaccagsasg | 58 |
| AD-63209 | A-126594.1 | csusgguaUfuUfCfCfuaggGfdTacaaL96 | 50 | A-126607.1 | usUfsgUfaCfcCfuAfggaAfaUfaCfcAfgsasg | 59 |
| AD-63223 | A-122745.16 | CfsusGfgUfaUfuUfCfCfCfuAfgGfgUfacCfaAfL96 | 51 | A-126612.1 | usUfsguaCfccuaggaAfaUfaccagsasg | 60 |
| AD-63226 | A-126589.1 | csusgguaUfuUfCfCfuaggGfuacaaL96 | 52 | A-122746.8 | usUfsgUfaCfcCfuAfgAfgaAfaUfaCfcAfgsasg | 61 |

TABLE 5

| | TMPRSS6 Single Dose Screen | |
|---|---|---|
| DuplexID | 10 nM Avg | 0.1 nM Avg |
| AD-63240 | 12.29 | 27.03 |
| AD-63209 | 17.11 | 23.38 |
| AD-63223 | 21.98 | 27.52 |
| AD-63226 | 18.36 | 41.65 |
| AD-60998 | 26.1 | 42.9 |

TABLE 6

In vivo Relative TMPRSS6 Message (% PBS) Modified Sequences based on AD-60940 (SEQ ID NOs: 11 and 12) (0.5 mg/kg, Day 14)

| Duplex ID | Sense sequence ID | Sense sequence | SEQ ID NO: | Antisense sequence ID | Antisense sequence | SEQ ID NO: | Aver. TMPRS6 mRNA (% PBS) | SD |
|---|---|---|---|---|---|---|---|---|
| AD-60940 | A-122745 | CfsusGfgUfaUfuUfCfCfuAfgGfgUfaCfaAfL96 | 62 | A-122746 | usUfsgUfaCfcCfuAfggaAfaUfacCfcAfgsasg | 87 | 47.47 | 10.13 |
| AD-63202 | A-126586 | Y44CfsusGfgUfaUfuUfCfCfuAfgGfgUfaCfaAfL96 | 63 | A-122746 | usUfsgUfaCfcCfuAfggaAfaUfacCfcAfgsasg | 88 | 50.01 | 3.32 |
| AD-64372 | A-122745 | CfsusGfgUfaUfuUfCfCfuAfgGfgUfaCfaAfL96 | 64 | A-128052 | VPusUfsgUfaCfcCfuAfggaAfaUfaCfcAfgsasg | 89 | 37.51 | 10.07 |
| AD-64373 | A-126586 | Y44CfsusGfgUfaUfuUfCfCfuAfgGfgUfaCfaAfL96 | 65 | A-128052 | VPusUfsgUfaCfcCfuAfggaAfaUfaCfcAfgsasg | 90 | 34.37 | 8.85 |
| AD-63223 | A-122745 | CfsusGfgUfaUfuUfCfCfuAfgGfgUfaCfaAfL96 | 66 | A-126612 | usUfsguaCfccuaggaAfaUfaccagsasg | 91 | 40.21 | 15.76 |
| AD-63240 | A-122745 | CfsusGfgUfaUfuUfCfCfuAfgGfgUfaCfaAfL96 | 67 | A-126607 | usUfsguaCfcCfuAfggaAfaUfaccagsasg | 92 | 50.63 | 11.01 |
| AD-64374 | A-126586 | Y44CfsusGfgUfaUfuUfCfCfuAfgGfgUfaCfaAfL96 | 68 | A-126607 | usUfsguaCfcCfuAfggaAfaUfaccagsasg | 93 | 55.48 | 14.32 |
| AD-64375 | A-126586 | Y44CfsusGfgUfaUfuUfCfCfuAfgGfgUfaCfaAfL96 | 69 | A-126612 | usUfsguaCfccuaggaAfaUfaccagsasg | 94 | 49.80 | 8.34 |
| AD-63209 | A-126594 | csusgguaUfuUfCfCfuaggGfdTacaaL96 | 70 | A-122746 | usUfsgUfaCfcCfuAfggaAfaUfaCfcAfgsasg | 95 | 29.21 | 1.57 |
| AD-64376 | A-126594 | csusgguaUfuUfCfCfuaggGfdTacaaL96 | 71 | A-126607 | usUfsguaCfcCfuAfggaAfaUfaccagsasg | 96 | 25.33 | 4.85 |
| AD-64377 | A-126594 | csusgguaUfuUfCfCfuaggGfdTacaaL96 | 72 | A-126612 | usUfsguaCfccuaggaAfaUfaccagsasg | 97 | 27.28 | 4.84 |
| AD-64378 | A-126594 | csusgguaUfuUfCfCfuaggGfdTacaaL96 | 73 | A-128053 | VPusUfsguaCfccuaggaAfaUfaccagsasg | 98 | 22.57 | 4.78 |
| AD-64379 | A-122745 | CfsusGfgUfaUfuUfCfCfuAfgGfgUfaCfaAfL96 | 74 | A-128054 | VPusuguaCfccuaggaAfaUfaccagsasg | 99 | 102.42 | 10.39 |
| AD-60940 | A-122745 | CfsusGfgUfaUfuUfCfCfuAfgGfgUfaCfaAfL96 | 75 | A-122746 | usUfsgUfaCfcCfuAfggaAfaUfacCfcAfgsasg | 100 | 44.19 | 9.18 |
| AD-63226 | A-126589 | csusgguaUfuUfCfCfuaggGfuacaaL96 | 76 | A-122746 | usUfsgUfaCfcCfuAfggaAfaUfaCfcAfgsasg | 101 | 38.16 | 5.70 |

TABLE 6-continued

In vivo Relative TMPRSS6 Message (% PBS) Modified Sequences based on AD-60940 (SEQ ID NOs: 11 and 12) (0.5 mg/kg, Day 14)

| Duplex ID | Sense sequence ID | Sense sequence | SEQ ID NO: | Antisense sequence ID | Antisense sequence | SEQ ID NO: | Aver. TMPRSS6 mRNA (% PBS) | SD |
|---|---|---|---|---|---|---|---|---|
| AD-64380 | A-126589 | csusgguaUfuUfCfCfcuaggGfuacaaL96 | 77 | A-126607 | usUfsguaCfccfuAfggaAfaUfaccagsasg | 102 | 34.38 | 5.31 |
| AD-64381 | A-126589 | csusgguaUfuUfCfCfcuaggGfuacaaL96 | 78 | A-126612 | usUfsguaCfccuaggaAfaUfaccagsasg | 103 | 36.09 | 8.17 |
| AD-64382 | A-126589 | csusgguaUfuUfCfCfcuaggGfuacaaL96 | 79 | A-128053 | VPusUfsguaCfccuaggaAfaUfaccagsasg | 104 | 27.54 | 9.17 |
| AD-64383 | A-126589 | csusgguaUfuUfCfCfcuaggGfuacaaL96 | 80 | A-128054 | VPusUfsguaCfccuaggaAfaUfaccagsasg | 105 | 80.90 | 13.10 |
| AD-64384 | A-128051 | Y44csusgguaUfuUfCfCfcuaggGfuacaaL96 | 81 | A-122746 | usUfsgUfaCfcCfuAfggaAfaUfaCfcAfgsasg | 106 | 32.13 | 2.64 |
| AD-64385 | A-128051 | Y44csusgguaUfuUfCfCfcuaggGfuacaaL96 | 82 | A-126607 | usUfsguaCfccfuAfggaAfaUfaccagsasg | 107 | 34.48 | 13.95 |
| AD-64386 | A-128051 | Y44csusgguaUfuUfCfCfcuaggGfuacaaL96 | 83 | A-126612 | usUfsguaCfccuaggaAfaUfaccagsasg | 108 | 30.55 | 5.90 |
| AD-64387 | A-128051 | Y44csusgguaUfuUfCfCfcuaggGfuacaaL96 | 84 | A-128053 | VPusUfsguaCfccuaggaAfaUfaccagsasg | 109 | 25.14 | 3.08 |
| AD-64388 | A-128051 | Y44csusgguaUfuUfCfCfcuaggGfuacaaL96 | 85 | A-128054 | VPusUfsguaCfccuaggaAfaUfaccagsasg | 110 | 93.68 | 20.72 |
| AD-64389 | A-126617 | gsgsUfuUfCfcfuAfgGfgUfaCfaAfL96 | 86 | A-128055 | VPusUfsgUfaCfCfuAfggaAfaUfaCfcasg | 111 | 28.30 | 1.76 |

Example 13. Further Modification of AD-60940

An additional series of duplexes containing sense and antisense strands based on the AD-60940 sequence were designed and paired using a combinatorial strategy to generate duplexes which were tested for activity in mice.

The ability of the duplexes to suppress expression of TMPRSS6 mRNA was assessed by measuring levels of TMPRSS6 mRNA in the liver of wild-type C57BL/6 mice following administration of the duplexes. A single dose of 3 mg/kg of each of the duplexes was administered subcutaneously and the mice were sacrificed on day 7 or day 21. The level of TMPRSS6 mRNA in the liver of the mice was measured by qPCR using the methods described above. A control group received injections with PBS. The duplexes and percent mRNA expression as compared to PBS injected mice are shown in Table 7 below.

The results demonstrate significant TMPRSS6 mRNA knockdown in mouse liver at day 7 by all of the duplexes tested.

TABLE 7

In vivo Relative TMPRSS6 Message (% PBS) Modified sequences based on AD-60940 (SEQ ID NOs: 11 and 12) (3 mg/kg, Day 7 and 21)

| Duplex ID | Sense seq ID | Sense sequence | SEQ ID NO: | Antinsense seq ID | Antisense sequence | SEQ ID NO: | Day 7 Aver. TMPRS6 mRNA | SD | Day 21 Aver. TMPRS6 mRNA | SD |
|---|---|---|---|---|---|---|---|---|---|---|
| AD-60940.1 | A-122745.1 | CfsusGfgUfaUfuUfCfCfcfuAfgGfgUfacfaAf L96 | 112 | A-122746.1 | usUfsgUfaCfcCfuAfggaAfaUfaCfcAfgsa sg | 128 | 9.38 | 1.72 | 18.37 | 5.98 |
| AD-64601.1 | A-129073.1 | csusggudAuuucdCuaggg(Tgn)acaaL96 | 113 | A-129067.6 | usdTsguacccudAggadAauaccagsasg | 129 | 62.73 | 11.68 | 60.75 | 12.51 |
| AD-64569.1 | A-129083.1 | csusgguadTuucdCuaggdAacaaL96 | 114 | A-129067.16 | usdTsguacccudAggadAauaccagsasg | 130 | 49.51 | 0.62 | 94.02 | 9.11 |
| AD-64604.1 | A-129074.2 | csusgguadTuucdCuaggg(Tgn)acaaL96 | 115 | A-129085.2 | usUsguacccudAggadAauaccagsasg | 131 | 27.12 | 1.58 | 43.69 | 2.85 |
| AD-64567.1 | A-126602.4 | csusgguauuucdCuaggg(Tgn)acaaL96 | 116 | A-129067.1 | usdTsguacccudAggadAauaccagsasg | 132 | 59.10 | 5.30 | 83.70 | 4.78 |
| AD-60940.1 | A-122745.1 | CfsusGfgUfaUfuUfCfCfcfuAfgGfgUfaCfaAf L96 | 117 | A-122746.1 | usUfsgUfaCfcCfuAfggaAfaUfaCfcAfgsa sg | 133 | 18.13 | 4.49 | 19.79 | 3.50 |
| AD-65104.1 | A-129875.1 | usgguadTuuccdTagggdTcaaaL96 | 118 | A-129876.1 | usdTsguaccccdTaggdAauaccasgsa | 134 | 97.90 | 5.59 | 97.26 | 10.65 |
| AD-64601.1 | A-129073.1 | csusggudAuuucdCuaggg(Tgn)acaaL96 | 119 | A-129067.6 | usdTsguacccudAggadAauaccagsasg | 135 | 57.17 | 5.03 | 54.34 | 4.07 |

TABLE 7-continued

In vivo Relative TMPRSS6 Message (% PBS) Modified Sequences based on AD-60940 (SEQ ID NOs: 11 and 12)(3 mg/kg, Day 7 and 21)

| Duplex ID | Sense seq ID | Sense sequence | Antinsense seq ID | Antisense sequence | SEQ ID NO: | Day 7 | | Day 21 | |
|---|---|---|---|---|---|---|---|---|---|
| | | | | | | Aver. TMPRS6 mRNA | SD | Aver. TMPRS6 mRNA | SD |
| AD-65105.1 | A-129073.2 | csusggudAuuucdCuaggg(Tgn)acaaL96 | A-129085.5 | usUsguacccudAggadAuauaccagsasg | 136 | 24.12 | 2.09 | 22.80 | 5.30 |
| AD-65106.1 | A-129073.2 | csusggudAuuucdCuaggg(Tgn)acaaL96 | A-129086.2 | usdTsguacccudAsggadAsauaccagsasg | 137 | 46.82 | 8.42 | 52.20 | 15.88 |
| AD-65107.1 | A-129710.1 | csusggudAuuucdCuagggdAacaaL96 | A-129067.18 | usdTsguacccudAggadAauaccagsasg | 138 | 46.07 | 4.14 | 61.63 | 5.68 |
| AD-65108.1 | A-129710.1 | csusggudAuuucdCuaggdAacaaL96 | A-129085.5 | usUsguacccudAggadAuauaccagsasg | 139 | 42.83 | 5.16 | 70.30 | 14.52 |
| AD-65109.1 | A-129710.1 | csusggudAuuucdCuaggdAacaaL96 | A-129086.2 | usdTsguacccudAsggadAsauaccagsasg | 140 | 45.67 | 11.75 | 64.56 | 5.09 |
| AD-65110.1 | A-130024.1 | csusggudAsuuucdCuaggg(Tgn)acaaL96 | A-129067.18 | usdTsguacccudAggadAauaccagsasg | 141 | 52.86 | 4.88 | 56.34 | 5.46 |
| AD-65111.1 | A-130024.1 | csusggudAsuuucdCuaggg(Tgn)acaaL96 | A-129085.5 | usUsguacccudAggadAuauaccagsasg | 142 | 28.16 | 6.90 | 26.50 | 3.95 |
| AD-65112.1 | A-130024.1 | csusggudAsuuucdCuaggg(Tgn)acaaL96 | A-129086.2 | usdTsguacccudAsggadAsauaccagsasg | 143 | 51.51 | 1.07 | 57.67 | 14.62 |

Example 14. Durability of Modified Duplexes Based on AD-60940

The durability of TMPRSS6 mRNA knockdown and transferrin saturation (TfSat) in response to treatment with the AD-60940-based duplexes were assayed in comparison to the parental duplex AD-60940. Wild-type C57BL/6 mice were administered a single dose of siRNA sufficient to result in about 70% knockdown of TMPRSS6 mRNA evaluated using qPCR as described above (i.e., 1.0 mg/kg of AD-60940; 3 mg/kg of AD-65105; 0.5 mg/kg of AD-64377). Mice were sacrificed at days 7, 14, 21, 28, 42, and 56 (n=3 per time point) and livers were harvested. Liver TMPRSS6 mRNA knockdown and transferrin saturation (TfSat) were assayed using the methods provided above. As shown in FIG. 8A, mRNA knockdown persisted through day 56 with both of the modified 60940-based duplexes tested. Similarly, a decrease in transferrin saturation was also observed through at least day 28 as shown in FIG. 8B.

The modified 60940-based duplexes were also analyzed in multidose studies in which two different doses of the duplexes were administered once per week for five weeks on days 0, 7, 14, 21, and 28; and samples were collected on days 14, 21, 28, and 35. As shown in FIGS. 9 A through D, a higher dose of the duplex resulted in an increased level of target knockdown and a larger decrease in the level of transferrin saturation with a trend towards a continued decrease in transferrin saturation at the last time point on day 35.

Example 15. Modification of AD-61002

A series of duplexes containing sense and antisense strands based on duplex AD-61002 sequences were designed and synthesized.

The ability of these modified duplexes to suppress expression of TMPRSS6 mRNA was assessed by measuring levels of TMPRSS6 mRNA in the liver of wild-type C57BL/6 mice following administration of the AD-61002-based duplexes. A single dose of 2 mg/kg of each of the duplexes was administered subcutaneously and the mice were sacrificed on day 21. Levels of TMPRSS6 mRNA in the liver were measured by qPCR using the methods described above. A control group received injections with PBS. The duplexes and percent mRNA expression as compared to PBS injected mice are shown in Table 8 below.

TABLE 8

In vivo Relative TMPRSS6 Message (% PBS) Modified Sequences based on AD-61002 (SEQ ID NOs: 19 and 20) (2.0 mg/kg, Day 21)

| Duplex ID | Sense sequence ID | Sense sequence (5' to 3') | SEQ ID NO: | Antisense sequence ID | Antisense sequence (5' to 3') | SEQ ID NO: | Aver. TMPRS6 mRNA (% PBS) | SD |
|---|---|---|---|---|---|---|---|---|
| AD-61002 | A-122838 | UfsgsGfuAfuUfuCfcCfCfUfaGfgGfuAfcAfaAfL96 | 144 | A-122839 | usUfsuGfuAfCfcUfaggAfaAfuAfcCfasgsa | 148 | 55.45 | 1.94 |
| AD-66014 | A-130086 | usgsguauUfuCfCfUfagggUfaAfcaaaL96 | 145 | A-130098 | usUfsuguAfcccuaggAfaAfuaccasgsa | 149 | 34.58 | 5.42 |
| AD-66015 | A-130087 | usgsguauUfuCfCfUfagggUfaAfacaaaL96 | 146 | A-130097 | usUfsuguAfcCfcuaggAfaAfuaccasgsa | 150 | 61.13 | 11.91 |
| AD-65189 | A-130093 | gsusauUfuCfCfUfagggUfacaaaL96 | 147 | A-130094 | usUfsuguAfcCfcuaggAfaAfuacscsa | 151 | 33.70 | 2.25 |

We claim:

1. A double stranded RNAi agent for inhibiting expression of TMPRSS6 in a cell, wherein said double stranded RNAi agent comprises a sense strand and an antisense strand forming a duplex, wherein the sense strand comprises the nucleotide sequence 5'-csusggudAsuuucdCuaggg(Tgn)acaa-3' (SEQ ID NO: 126) and the antisense strand comprises the nucleotide sequence 5'-usUsguacccudAggadAauac-cagsasg-3' (SEQ ID NO: 142), wherein a, c, g, and u are 2'-O-methyl (2'-OMe) A, C, G, and U; U is uridine-3'-phosphate; s is a phosphorothioate linkage; dA is 2'-deoxyadenosine; dC is 2'-deoxy-cytosine; and (Tgn) is thymidine-glycol nucleic acid (GNA)S-Isomer;

wherein the sense strand is 21 nucleotides in length and the antisense strand is 23 nucleotides in length; and wherein the double stranded RNAi agent is conjugated to a ligand.

2. The double stranded RNAi agent of claim 1, wherein the ligand is one or more GalNAc derivatives attached through a bivalent or trivalent branched linker.

3. The double stranded RNAi agent of claim 1, wherein the ligand is

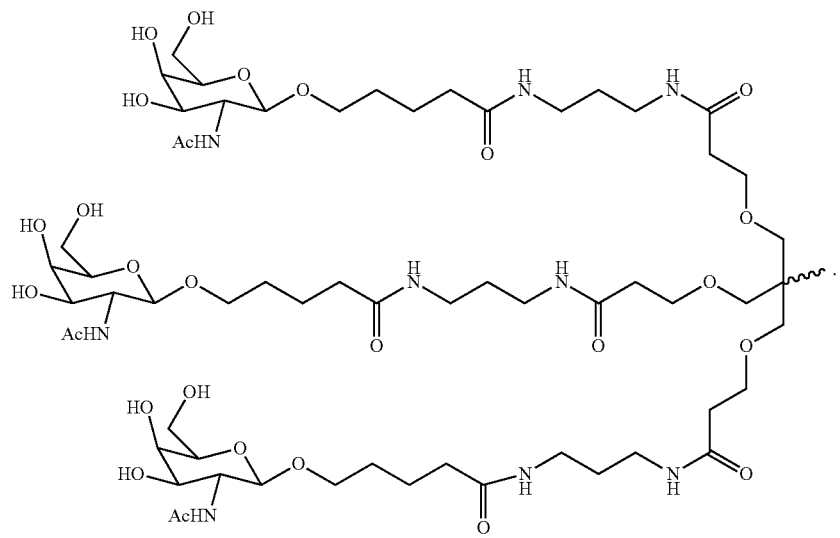 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

4. The double stranded RNAi agent of claim 1, wherein the ligand is attached to the 3' end of the sense strand.

5. The double stranded RNAi agent of claim 4, wherein the RNAi agent is conjugated to the ligand as shown in the following schematic

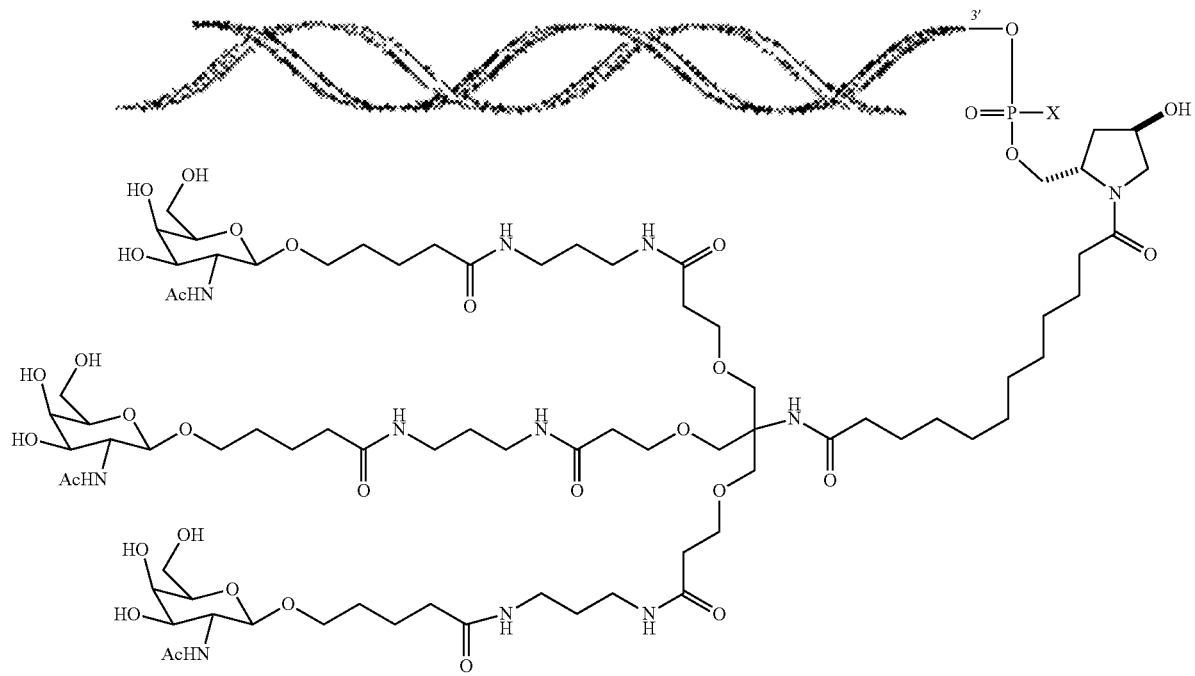

wherein X is O or S.

6. A pharmaceutical composition comprising the double stranded RNAi agent of claim 1.

7. A method of inhibiting TMPRSS6 expression in a cell, the method comprising:

(a) contacting the cell with the double stranded RNAi agent of claim 1, or the pharmaceutical composition of claim 6; and (b) maintaining the cell produced in step (a) for a time sufficient to obtain degradation of the mRNA transcript of a TMPRSS6 gene, thereby inhibiting expression of the TMPRSS6 gene in the cell.

8. The method of claim 7, wherein said cell is within a subject.

9. The method of claim 8, wherein the subject is a human.

10. The method of claim 7, wherein TMPRSS6 expression is inhibited by at least about 30%, about 40%, about 50%, about 60%, about 70%, about 80%, about 90%, about 95%, about 98% or about 100%.

11. The method of claim 8, wherein serum hepcidin concentration in said subject is increased by at least about 10%; and/or wherein serum iron concentration in said subject is decreased by at least about 20%; and/or wherein a percent transferrin saturation in said subject is decreased by at least about 20%.

12. A method of treating a subject having a TMPRSS6 associated disorder, comprising administering to the subject a therapeutically effective amount of the double stranded RNAi agent of claim 1, or the pharmaceutical composition of claim 6, thereby treating the subject.

13. The method of claim 12, wherein the subject is a human.

14. The method of claim 13, wherein the human has hereditary hemochromatosis, β-thalassemia, or erythropoietic porphyria.

15. The method of claim 13, wherein the human has a disorder associated with iron overload.

16. The method of claim 12, wherein the double stranded RNAi agent is administered to the subject subcutaneously; or intravenously.

17. The method of claim 12, further comprising administering an iron chelator to the subject.

* * * * *